Figure 3:
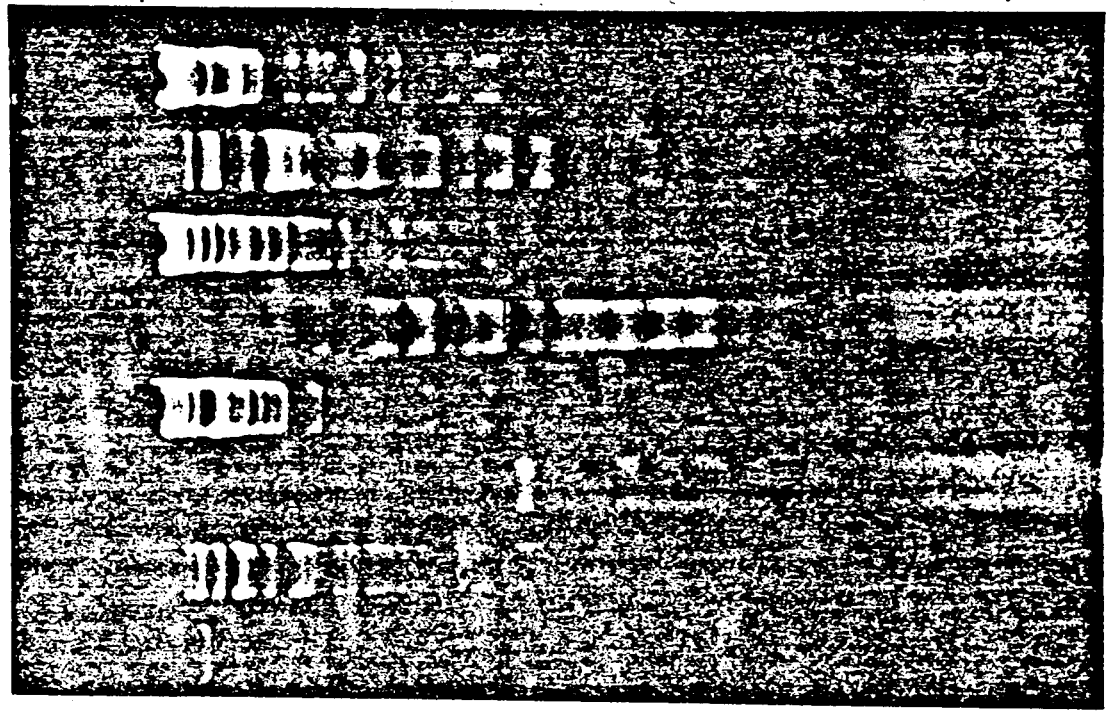

United States Patent [19]

Baseman et al.

[11] Patent Number: 5,026,636
[45] Date of Patent: Jun. 25, 1991

[54] METHODS AND COMPOSITIONS FOR PRODUCTION OF MYCOPLASMAL ADHESINS

[75] Inventors: Joel B. Baseman; C. J. Su; S. F. Dallo, all of San Antonio, Tex.

[73] Assignee: The University of Texas Board of Regents, Austin, Tex.

[21] Appl. No.: 118,967

[22] Filed: Nov. 10, 1987

[51] Int. Cl.$^5$ .................... C12Q 1/68; C12N 1/21; C12N 15/31
[52] U.S. Cl. ........................... 435/6; 435/69.1; 435/71.1; 435/91; 435/172.1; 435/172.3; 435/252.3; 435/320.1; 536/27; 935/6; 935/8; 935/9; 935/12; 935/22; 935/29; 935/59; 935/60; 935/72; 935/77; 935/79
[58] Field of Search ............... 536/27; 435/670, 172.3, 435/252.3, 320, 870, 69.1, 69.3, 71.1, 91, 170, 172.1, 172.3; 935/9, 11, 12, 22, 60, 72, 6, 8, 24, 59, 77, 79

[56] References Cited

PUBLICATIONS

Manicitis et al., 1982, Molecular Cloning, p.n-x, Cold Spring Harbor Laboratory.
Young and Davis, "Efficient Isolation of Genes by Using Antibody Probes", Proc. Natl. Acad. Sci, U.S.A., 80:1194-1198 (Mar. 1983).
Plummber et al., Infect. Immun., 53:398-403 (1986).
Trevino et al., Infect. Immun., 53:129-134 (1986).
Jacobs et al., Journal of General Microbiology, 133: 2233-2236 (2987).
Plummer et al., Infec. Immun., 55:49-56 (1987).
Kahane et al., Infect. Immun., 49:457-458 (1985).
Henikoff, Elsevier Science Publishers, 28:351-359 (1984).
Leith and Baseman, Journal of Bacteriology, 157:678-680 (1984).
Baseman et al., Molecular Basis of Oral Microbial Adhesin, Ed. Mergenhagen, pp. 18-23 (1985).
Morrison-Plummer et al., Journal of Immunological Methods, 64:165-178 (1983).
Krause and Baseman, Infect. Immun., 39:1180-1186 (1983).
Krause et al., Infect. Immun., 39:830-836 (1983).
Leith et al., Journal of Experimental Medicine, 157:502-504 (1983).
Krause et al., Infect. Immun., 35:809-817 (1982).
Baseman et al., Journal of Bacteriology, 151:1514-1522 (1982).
Messing et al., Nucleic Acids Research, 9:309-321 (1981).

Primary Examiner—Richard A. Schwartz
Assistant Examiner—Richard C. Peet
Attorney, Agent, or Firm—Arnold, White & Durkee

[57] ABSTRACT

The molecular cloning and nucleotide sequence of the complete structural gene encoding *Mycoplasma pneumoniae* P1 cytadhesin and the amino acid sequence of teh P1 protein is described. The present invention provides recombinant DNA clones encoding the complete P1 protein as well as clones expressing P1 polypeptides with cytadhesin epitopes. The substantially purified nucleic acid molecular recombinant vectors, recombinant cells, and recombinant polypeptides of the present invention are useful as hybridization probes and immunodiagnostic reagents and may be used to prepare anti-mycoplasmal vaccines.

44 Claims, 22 Drawing Sheets

FIG.2

```
              1     2     3     4     5     6
PROTEIN   NH2-Asn - Ala - Ile - Asn - Pro - Arg m-RNA     5' AAU  GCX  AUU  AAU  CC 3'---
                  C         C    C
                                 A
PROBE     3' TTA  CGX  TAA  TTG  GG 5'
                  G         G    A
                            T
```

```
              7     8     9    10    11    12
PROTEIN   Leu - Thr - Pro - Trp - Thr - Tyr m-RNA     5' CUX  ACX  CCX  UGG  ACX  UAU 3'
             U              A         C

PROBE     3' GAX  TGX  GGX  ACC  TGX  ATA 5'
             A                   T    G
```

```
             13    14    15    16    17    18
          Arg - Asn - Thr - Ser - Phe - Ser
```

LEGEND:
- B = BamHI
- E = EcoRI
- EV = EcoRV
- H = HindIII
- K = KpnI
- P = PstI
- S = SmaI
- SA = SalI
- SC = SacI

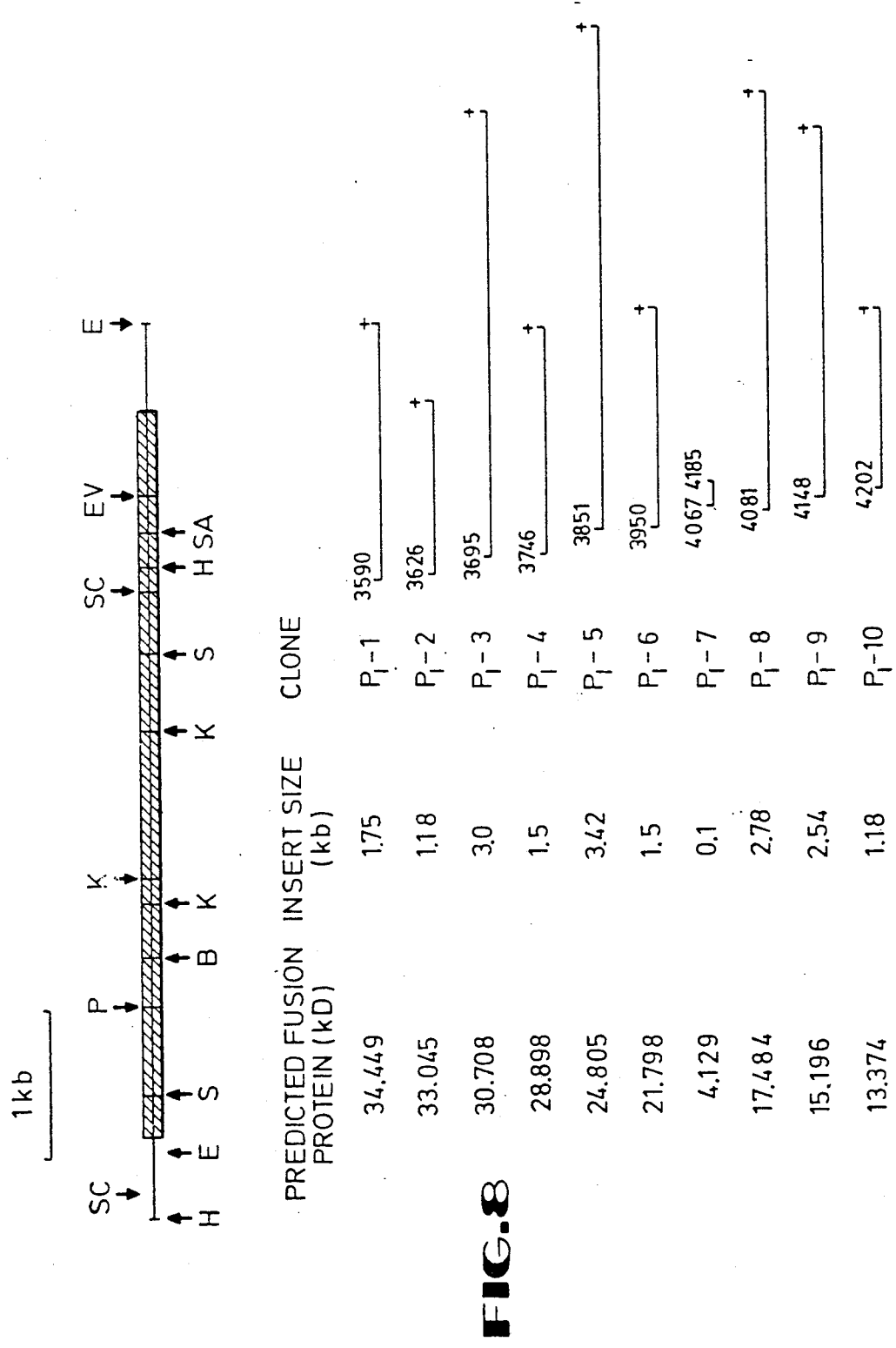

```
                                                                                  3960
AAC CTC AGT AGT GTG CTT AGT GGT GCT GGG GGT GGA GGG GGT TCT TCA GGC TCA GGT CAA
Asn Leu Ser Ser Val Leu Ser Gly Ala Gly Gly Gly Gly Gly Ser Ser Gly Ser Gly Gln
                              3930                                                4020
TCT GGC GTG GAT CTC TCC CCC GTT GAA AAA GTG AGT GGG TGG CTT GTG GGG CAG TTA CCA
Ser Gly Val Asp Leu Ser Pro Val Glu Lys Val Ser Gly Trp Leu Val Gly Gln Leu Pro
                              3990                                                4080
AGC ACG AGT GAC GGA AAC ACC TCC TCC ACC AAC CTC GCG CCT AAT ACT AAT ACG GGG
Ser Thr Ser Asp Gly Asn Thr Ser Ser Thr Asn Leu Ala Pro Asn Thr Asn Thr Gly
                              4050                       ▼
                                                                                  4140
AAT GAT GTG GTG GGG GTT GGT CGA CTT TCT GAA AGC CTG AAC GCC GCA AAG ATG AAT GAC GAT
Asn Asp Val Val Gly Val Gly Arg Leu Ser Glu Ser Leu Asn Ala Ala Lys Met Asn Asp Asp
                              4110                                                4200
         GTT GAT ATT GTA CGC ACC CCA CTC GCT GAA CTG TTA GAT GGG GAA CAA ACA GCT
         Val Asp Ile Val Arg Thr Pro Leu Ala Glu Leu Leu Asp Gly Glu Gln Thr Ala
         *                    4170                        ▲
                                                                                  4260
▽ GAC ACT GGT CCA CAA AGC GTG AAG TTC TCT CCT GAC CAA ATT GAC TTC AAC CGC TTG
  Asp Thr Gly Pro Gln Ser Val Lys Phe Ser Pro Asp Gln Ile Asp Phe Asn Arg Leu
                              4230
```

FIG.9A

```
                                                        4290                                                                4320
TTT ACC CAC CCA GTC ACC GAT CTG TTT GAT CCG GTA ACT ATG TTG GTG TAT GAC CAG TAC
Phe Thr His Pro Val Thr Asp Leu Phe Asp Pro Val Thr Met Leu Val Tyr Asp Gln Tyr 4350                                                                4380
ATA CCG CTG TTT ATT GAT ATC CCA GCA AGT GTG AAC CCT AAA ATG GTT CGT TTA AAG GTC
Ile Pro Leu Phe Ile Asp Ile Pro Ala Ser Val Asn Pro Lys Met Val Arg Leu Lys Val 4410                                                                4440
TTG AGC TTT GAC ACC AAC GAA CAG AGC TTA GGT CTC CGC TTA GAG TTC TTT AAA CCT GAT
Leu Ser Phe Asp Thr Asn Glu Gln Ser Leu Gly Leu Arg Leu Glu Phe Phe Lys Pro Asp 4470                                                                4500
CAA GAT ACC CAA CCA AAC AAC GTT CAG AAT CCG GTC AAT GGT GAC TTC TTA CCA
Gln Asp Thr Gln Pro Asn Asn Val Gln Asn Pro Val Asn Gly Asp Phe Leu Pro 4530                                                                4560
CTG TTA ACG GCC TCC AGT CAA GGT CCC CAA ACC TTG TTT AGT CCG TTT AAC CAG TGA CCT
Leu Leu Thr Ala Ser Ser Gln Gly Pro Gln Thr Leu Phe Ser Pro Phe Asn Gln Trp Pro
```

FIG.9B

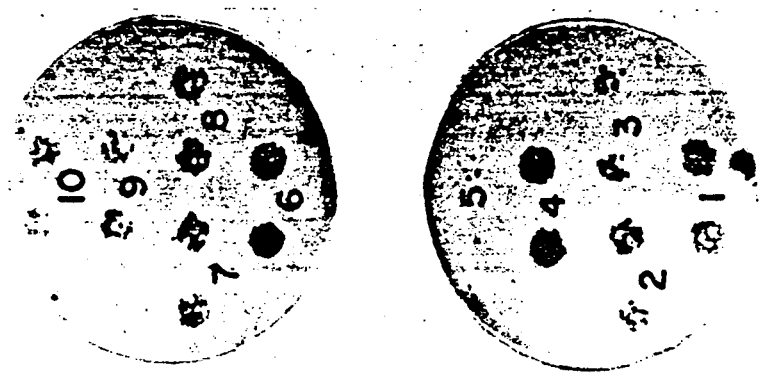
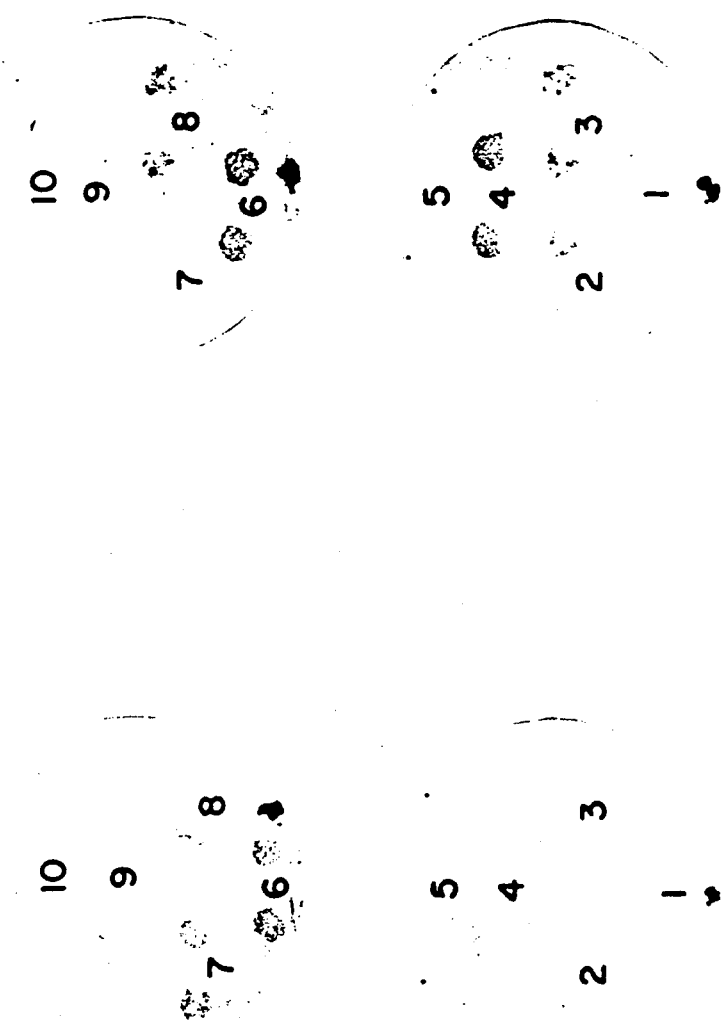
FIG. 12-III  FIG. 12-II  FIG. 12-I

```
TTAAGGCATCATTGCCTTAATTGCATGCGCTTCATCGAAATTTCATCACCACCGCCCCCAGTATAAGTCCGTCGCCACG
AATTCCGTAGTAACGGAATTAACGTACGCGCGAAGTAGCGTTTAAAGTATGGTGGCGGGGGTCATATTCAGGCCGGTGC
                                                                              60
TCAAGAATTTCGTTCGCGCTGTATTAAGCACATCAAGTTCTAACGTTTTCGTTTAACGACATATTAAAAATTGTTGA
AGTTCTTAAAGCAAGCGCGACATAATTCGTGTAGTTTCAAGATTGCCAAAAGCAAATTGCTGTATAATTTTAACAACT

TAC GTG GTT TGG TTT TTT TGA CGG AAC AGG TTC AGG TGA ACC TAA GAG TAG GAG TGG CGG
ATG CAC CAA ACC AAA AAA ACT GCC TTG TCC AAG TCC ACT TGG ATT CTC ATC CTC ACC GCC
Met His Gln Thr Lys Lys Thr Ala Leu Ser Lys Ser Thr Trp Ile Leu Ile Leu Thr Ala
                    30                                                       120

TGG CGG AGG GAG CGC TGC CCT GAG TGG CAT CAC CCT GTG AAG TGT TCA TGG TGG TGC TGC
ACC GCC TCC GCG CTC ACG GTA GTG GGA CAC TTC ACA AGT ACC ACG ACG ACG
Thr Ala Ser Leu Ala Thr Gly Leu Thr Val Val Gly His Phe Thr Ser Thr Thr Thr Thr
                    90                                                       180

GAG TTC GCG GTC GTT AAA TCG ATG TGG GCG GGA CTG CTC CAG CGC GAC GCG GTG TGG TTA
CTC AAG CGC CAG CAA TTT AGC TAC ACC CCT GAC CGC GAG GTC CGC CTG CAC ACC AAT
Leu Lys Arg Gln Gln Phe Ser Tyr Thr Arg Pro Asp Leu Ala Leu Arg His Thr Asn
                   150                                                       240

CGG TAG TTG GGC GCG AAT TGG GGC ACT TGC ATA GCA TTG TGC TCG AAA AGG AGG GAG GGG
GCC ATC AAC CCG CGC CGC TTA ACC CCG TGA ACG CGT TAT AAC ACG AGC TTT TCC TCC CCC
Ala Ile Asn Pro Arg Leu Thr Pro Trp Tyr Arg Asn Thr Ser Phe Ser Ser Leu Pro
                   210                                                       300

GAG TGC CCA CTT TTA GGG CCC CGC ACC CGG AAT CAC GCG CTG TTG TCG CGA TTC CCG TAG
CTC ACG GGT GAA AAT CCC GGG GCG TGG CGC GCC TTA GTG CGC GAC AGC AGC GCT AAG GGC ATC
Leu Thr Gly Glu Asn Pro Gly Ala Trp Ala Leu Val Arg Asp Asn Ser Ala Lys Gly Ile
                   270
```

FIG.6A

```
                                          330                                          360
TGA CGG CCG TCA GTT GTT TGG ATA CTA GGG TGC ATA CTA GGG TGG GCT TGG CTT CGC CGA AAC
ACT GCC GGC AGT CAA CAA ACC TAT GAT CCC ACG CAA CCC ACC CGA GAA GCG TTG
Thr Ala Gly Ser Gln Gln Thr Thr Tyr Asp Pro Thr Arg Thr Arg Glu Ala Ala Leu
                                          390                                          420
TGG CGT AGT TGG TGG AAA CGC AAT GCG GCC ATA CTG GAG CGG CCC GCG CGG AAT ATG CTG
ACC GCA TCA ACC ACC TTT GCG TTA CGC TAT GAC CTC GCC CGC GCC TTA TAC GAC
Thr Ala Ser Thr Thr Phe Ala Leu Arg Arg Tyr Asp Leu Ala Gly Arg Ala Leu Tyr Asp
                                          450                                          480
GAG CTA AAA AGC TTC AAT TTG GGC GTT TGC GGG TGC CTG GTT TGG CCC GTC TAG TGG
CTC GAT TTT TCG AAG TTA AAC CCG CAA ACG CGC GAC CAA ACC GGG CAG ATC ACC
Leu Asp Phe Ser Lys Leu Asn Pro Gln Thr Arg Asp Leu Ala Gly Arg Ala Leu Tyr Asp
                                    Pro Gln Thr Arg Asp Pro Gln Gln Thr Gly Gln Ile Thr
                                          510                                          540
AAA TTG GGG AAA CCG AAA CCA TCA CCC CGA CGT GCA CGT GTT GTC ACT TTG CTC CAG
TTT AAC CCC TTT GGC GGC TTT GGT AGT GGG GCT CAG CAG TGA AAC GAG GTC
Phe Asn Pro Phe Gly Gly Phe Leu Ser Gly Ala Ala Pro Gln Gln Trp Asn Glu Val
                                          570                                          600
TTT TTC CAG GGG CAG CTC CAC CGC CGT GTT CTG GGG AGG TTA GGG ATG GCC AAA CGG CAA
AAA AAG GTC CCC GTC GAG GTG GCG CAA GAC CCC AAT TCC CCC TAC CGG TTT GCC GTT
Lys Asn Lys Val Pro Val Ala Gln Asp Pro Ser Asn Pro Tyr Arg Phe Ala Val
                                          630                                          660
AAT GAG CAC GGC GCG TCG CAC CAC ATG ATA CTC GTC AAC GTT TCC CCC AAC CCG AAT GGT
TTA CTC CCG CCG CGC AGC GTG GTG TAC TAT GAG CAG TTG CAA AGG GGG TTG GGC TTA CCA
Leu Leu Val Pro Arg Ser Val Val Tyr Tyr Glu Gln Leu Leu Asn Gly Arg Gly Leu Pro
```

FIG.6B

```
                                                                           720
     GTC GCT TGG CTC TCA CCA GTT CAA CCT TTA AGG TGA TAC CCC CGT TAC AAA CCG AAC TTC
     CAG CAG CGA GAG AGT GGT CAA AGT AAT ACT TCC ACC ATG GGG GCA ATG TTT GGC TTG AAG
     Gln Gln Arg Glu Ser Gly Gln Ser Asn Thr Ser Thr Met Gly Ala Met Phe Gly Leu Lys
  690

780
     CAC TTG CGG CTC CGC CTG TGG CGC CTG TGG CTT TCG TTA CTT GAA AAA CCC CGG CTC CGG
     GTG AAC GCC TCA ACA TGG AAG GTC AAA AGC AGC AAT GAA AAG CAG GGG GCC GAG GCT GCC
     Val Asn Ala Ala Thr Trp Lys Val Lys Ser Ser Asn Glu Lys Gln Gly Ala Glu Ala Ala
                750

840
     TGA CCA AGA AGT TGG TGT AGA CCT TTT TAT CGA AAT CGG GTT GCA CCC CCA AGC AGT CCC
     ACT AGT TCT TCA ACA AGA TCT GAA ATA TTA AAA TGG CAA CGT GGG GGT CAG CGG TCA GGG
     Thr Ser Ser Ser Thr Arg Ser Glu Ile Leu Lys Trp Gln Arg Gly Gly Gln Arg Ser Gly
            810

900
     CTG TGG TTT CAG TTC AAG TTA CTT TTT ATT CAC TTT AAA AAG TAA CGA TTC GCC TCG CTC
     GAC ACC AAA GTC AAG TTA TTT CAA AAT AGT GAG GTG AAA AAG ATT AAG CGG AGC GAG GAC
     Asp Thr Lys Val Lys Leu Phe Gln Asn Ser Glu Val Lys Lys Ile Lys Arg Ser Glu Asp
                        870

960
     CCA GTC GAC GTC AAT CTT TTT AAA AAT CTA GAG CGG TTG AAC GCC TTG AAG CGG CTT GCC
     GGT CAG CAG CTG TTA GAA AAA TTT GAT CTC AAG TTC CGC AAC ATT CCC AGC TCC GAG AGC
     Gly Gln Gln Leu Leu Glu Lys Phe Asp Leu Lys Phe Arg Asn Ile Pro Ser Ser Glu Glu
                                930

1020
     AGC CCA GTC AGG CAG GTT GAG TTC CGC GAC CTG CTA AAA CCA TGA CGG GAA AGG TCA CCT
     TCG GGT CAG TCC GTC CAA CTC AAG GCG GAT TTT GGT ACT TCC ACT GCC CTT AGT TCG GGA
     Ser Gly Gln Ser Val Gln Leu Lys Ala Asp Phe Gly Thr Ala Leu Lys Ser Ser Ser Gly
                                        990

FIG.6C
```

```
                                                             1080
AGT CCG TTG AGG TTA GGG CCA AGG TCC GGG ACT TCC GGG ACT TCC GGA ACC GAA CGC TGA CTC
TCA GGC AAC TCC AAT CCC GGT CCC CCG GGT TGA AGG CCC TGA CCC CGG CTT GCG ACT GAG
Ser Gly Asn Ser Asn Pro Gly Ser Pro Thr Pro Trp Arg Pro Trp Leu Ala Thr Glu

1140
GTT TAA GTG TTC CTG GAG GGG TTT ACT AGG CGG TAA GAC ATG CTA CGC GGA
CAA ATT CAC AAG GAC CTC CCC AAA TGA TCC GCC TCG ATC CTG TAC GAT GCG CCT
Gln Ile His Lys Asp Leu Pro Lys Trp Ser Ala Ser Ile Leu Tyr Asp Ala Pro

1200
ATA CGC GCG TTG GCA TGG CGG CAA CTG GCG AAC CTA GTG TTC CGG TAC TGG
TAT GCG CGC AAC CGT ACC CGT GTT CGC GAC CAT CAC TTG AAG GCC ATG ACC
Tyr Ala Arg Asn Arg Thr Ala Ile Asp Arg Val Asp His Leu Asp Pro Lys Ala Met Thr

1260
CGC TTG ATA GGC GGG TCA ACT TCT TGC GGG TTC ACT TTG GTG CCA AAC ACC CTG ACT
GCG AAC TAT CCG CCC AGT TGA AGA ACG CCC AAG TGA AAC CAC GGT TTG TGG GAC TGA
Ala Asn Tyr Pro Pro Ser Thr Arg Thr Pro Lys Phe Thr Leu Val His Gly Leu Trp Asp Trp

1320
TTC CGC GCG CTA CAA AAC GAG GTT TGG TGG CCC AAG AAG TTG GGC GCG GTG CAC CCC GAG
AAG GCG CGC GAT GTT TTG CTC CAA ACC ACC GGG TTC TTC AAC CCG CGC CAC GTG GGG CTC
Lys Ala Arg Asp Val Leu Leu Gln Thr Thr Gly Phe Phe Asn Pro Arg His Pro Glu

1380
ACC AAA CTA CCG CCC GTC TGC CAG CGC CGG GGG CTA TTG CTT TTC CCC AAA CTA CAC TTG
TGG TTT GAT GGC GGG CAG ACG GTC GCG GCG GAT AAC GAA AAG GGG TTT GAT GTG AAC
Trp Phe Asp Gly Gly Gln Thr Val Ala Asp Asn Gly Lys Thr Gly Phe Asp Val Asp Asn
```

FIG. 6D

```
                    2850                    2880
Asn  Ile  Ser  Lys  Gly  Asp  Ser  Thr  Gln  Asp  Gly  Asn  Ala  Ile  Asp  Gln  Gln
TTA  TAA  TCA  TTC  TCA  CCC  CTA  TCA  AAT  TGG  GTC  CTG  CCG  TTA  CGC  TAG  CTA  GTT  GTT
AAT  ATT  AGT  AAG  AGT  GGG  GAT  AGT  TTA  TGC  CAG  GAC  GGC  AAT  GCG  ATC  GAT  CAA  CAA 2910                    2940
Glu  Ala  Thr  Asn  Tyr  Thr  Asn  Leu  Pro  Pro  Asn  Leu  Thr  Pro  Ala  Asp  Trp  Pro  Asn
CTC  CGG  TGG  ATG  TGG  TTG  GAG  GGG  TTG  GAG  TGG  CGA  CTA  ACT  GGC  TTG
GAG  GCC  ACC  TAC  ACC  AAC  CTC  CCC  AAC  CCC  ACC  GCT  GAT  TGA  CCG  AAC 2970                    3000
Ala  Leu  Ser  Phe  Ile  Pro  Val  Leu  Val  Asn  Lys  Asn  Ala  Gln  Arg  Ala  Gln  Leu  Phe  Leu  Arg  Gly  Leu
CGC  GAC  AGT  AAG  TGG  TTC  TTG  CGC  GTC  GCG  CGG  GTC  GAG  AAG  GAG  GCG  CCG  AAG
GCG  CTG  TCA  TTC  CCG  ATC  AAC  AAG  GTG  CAG  GCC  CAG  CTC  CTC  CGC  GGC  TTG 3030                    3060
Leu  Gly  Ser  Ile  Pro  Arg  Ser  Asp  Gly  Ser  Arg  Ala  Gln  Leu  Arg  Gly  Leu
AAC  CCG  TCG  TAG  GGC  CAC  AAC  CAC  TTA  GCT  TCA  CCC  AGG  TCA  CCC  AGG  TTG  TTT  AAG  GTT  CGG
TTG  GGC  AGC  ATC  CCG  GGC  GTG  TTG  AAT  CGA  AGT  GGG  TCC  AAC  TTC  AAC  CTG  CAA  GCC 3090                    3120
Thr  Asp  Gln  Lys  Trp  Tyr  Thr  Ser  Asp  Leu  His  Ser  Asp  Gln  Thr  Lys  Leu  Asn  Leu  Pro
TGG  CTG  GTT  TTT  ACC  AGG  ATG  TGG  CTG  AAT  GTA  AGC  CTG  GTT  TGG  TTT  GAC  TTG  GAG  GGG
ACC  GAC  CAA  AAA  TGG  TCC  TAC  ACC  GAC  TTA  CAT  TCG  GAC  CAA  ACC  AAA  CTG  AAC  CTC  CCC 3150                    3180
Ala  Tyr  Gly  Glu  Val  Asn  Gly  Leu  Leu  Leu  Asn  Pro  Ala  Leu  Val  Glu  Thr  Tyr  Phe  Gly  Asn
CGA  ATG  CCA  CTC  CAC  TTA  CCC  AAC  AAC  TTA  GGC  CGC  AAC  CAC  CTT  TGG  ATA  AAA  CCC  TTG
GCT  TAC  GGT  GAG  GTG  AAT  GGG  TTG  TTG  AAT  CCG  GCG  TTG  GTG  GAA  ACC  TAT  TTT  GGG  AAC
```

FIG. 6I

```
TGC GCT CGC CCA CCA AGC CCC AGG TTG TGC TGG TCA AGT GGG CCA TAG CCA AAA TTT TAA
ACG GCG CGA GGT GGT TCG GGG TCC AAC ACG ACC AGT TCA CCC GGT ATC GGT TTT AAA ATT
Thr Arg Ala Gly Gly Ser Gly Ser Asn Thr Thr Ser Ser Pro Gly Ile Gly Phe Lys Ile
                                      3210                                 3240

GGG CTT GTT TTA CTA AGG TTT CGG TGG GAC TGG TAG TGG GGG CCC AAC CGA ACT TGC GGG
CCC GAA CAA AAT GAT TCC AAA GCC ACC CTG ATC AGT ACC CCC GGG TTG GCT TGA ACG CCC
Pro Glu Gln Asn Asp Ser Lys Ala Thr Leu Ile Ser Thr Pro Gly Leu Ala Trp Thr Pro
                                      3270                                 3300

GTC CTG CAG CCA TTG GAG CAA CAG TCA CCG TGG TGC CAG TCG AAG GTC GAG CCA CCC ACC
CAG GAC GTC GGT AAC CTC GTT GTC AGT GGC ACC GTG AGC TTC CAG CTC GGC GGG TGG
Gln Asp Val Gly Asn Leu Val Val Ser Gly Thr Val Ser Phe Gln Leu Gly Gly Trp
                                      3330                                 3360

GAC CAG TGG AAG TGC CTG AAA CAG TTT GGG GCG CGC CCA ATG GAG CCA GAG GTC AAT TGC
CTG GTC ACC TTC ACG GAC TTT GTC AAA CCC GCG CGC GGT TAC CTC GGT CTC CAG TTA ACG
Leu Val Thr Phe Thr Asp Phe Val Lys Pro Ala Arg Gly Tyr Leu Gly Leu Gln Leu Thr
                                      3390                                 3420

CCG AAC CTA CGT TCA CTA CGT TGC GTC CAG TTG CGG GAG TAA ACC CGG GGG ACT CGC
GGC TTG GAT GCA AGT GAT GCG CAG ACG GCG CGC GCC GCT ATT TGG GCC CCC TGA GCG
Gly Leu Asp Ala Ser Asp Ala Thr Arg Ala Arg Ala Ala Ile Trp Ala Pro Trp Ala
                                      3450                                 3480

CGG AAA GCA CCG TCA ACC CAG TTG GCC AAC CCG CAC CTC TCA CAC ACC CTA AAC TTC
GCC TTT CGT GGC AGT TGG GTC AAC CGG TTG GTC GCG GAG AGT GTG TGG GAT TTG AAG
Ala Phe Arg Gly Ser Trp Val Asn Arg Leu Gly Arg Val Glu Ser Val Trp Asp Leu Lys
                                      3510                                 3540
```

FIG. 6J

FIG. 6E

```
                                                              1410                                                                        1440
AGA  CTT  TTG  TGG  TTC  GTC  CCG  AAA  GTT  TTC   CTT  CGA  CTG  AGG  CTG  TTC  AGC  CGG  GGC  TAG
TCT  GAA  AAC  ACC  AAG  CAG  GGC  TTT  CAA  AAG   GAA  GCT  GAC  TCC  GAC  AAG  TCG  CCC  CCG  ATC
Ser  Glu  Asn  Thr  Lys  Gln  Gly  Phe  Gln  Lys   Glu  Ala  Asp  Ser  Asp  Lys  Ser  Ala  Pro  Ile 1470                                                                        1500
CGG  GAG  GGC  AAA  CAC  CTT  CGC  ATG  AAG  CGG   TTG  TAA  CCG  TTG  GAG  TGG  ACC  AAG  CCC  GTT  CGC
GCC  CTC  CCG  TTT  GTG  GAA  GCG  TAC  TTC  GCC   AAC  ATT  GGC  AAC  CTC  ACC  TGG  TTC  GGG  CAA  GCG
Ala  Leu  Pro  Phe  Val  Glu  Ala  Tyr  Phe  Ala   Asn  Ile  Gly  Asn  Leu  Thr  Trp  Phe  Gly  Gln  Ala 1530                                                                        1560
GAA  AAC  CAC  CCA  CCG  TTA  CCG  GTA  CAA  TGG   TTC  AGC  CGG  GTG  TGG  CGC  GGA  AAC  TCA
CTT  TTG  GTG  GGT  GGC  AAT  GGC  CAT  GTT  CAA   AAG  TCG  GCC  CAC  ACC  GCG  CCT  TTG  AGT
Leu  Leu  Val  Gly  Gly  Asn  Gly  His  Val  Thr   Lys  Ser  Ala  His  Thr  Ala  Pro  Leu  Ser 1590                                                                        1620
TAT  CCA  CAG  AAA  TCC  CAC  GCG  ATA  TTA  CGT   TGA  CCT  TGG  TCA  CGA  CAT  TGA  CCA  ACT
ATA  GGT  GTC  TTT  AGG  GTG  CGC  TAT  AAT  GCA   ACT  GGT  ACC  AGT  GCT  GTA  ACT  GGT  TGA
Ile  Gly  Val  Phe  Arg  Val  Arg  Tyr  Asn  Ala   Thr  Gly  Thr  Ser  Ala  His  Thr  Gly  Trp 1650                                                                        1680
GGT  ATA  AAT  GAC  AAG  AGT  CCG  TAC  CAG  TTG   TTT  GTT  AAC  CAA  ATG  GTC  CCC  AAT  TTC  CTA  GAT
CCA  TAT  TTA  CTG  TTC  TCA  GGC  ATG  GTC  AAC   AAA  CAA  TTG  GTT  TAC  CAG  GGG  TTA  AAG  GAT  CTA
Pro  Tyr  Leu  Leu  Phe  Ser  Gly  Met  Val  Asn   Lys  Gln  Thr  Asp  Gly  Leu  Lys  Asp  Leu 1710                                                                        1740
GGG  AAA  TTG  TTA  TTG  GCG  ACC  AAA  CTT  ATA   CAT  GGT  GCC  TAC  CGT  CAA  CGA  CCG  CGA  TTC
CCC  TTT  AAC  AAT  AAC  CGC  TGG  TTT  GAA  TAT   GTA  CCA  CGG  ATG  GCA  GTT  GCT  GGC  GCT  AAG
Pro  Phe  Asn  Asn  Arg  Trp  Phe  Glu  Tyr  Val   Pro  Arg  Met  Ala  Val  Ala  Gly  Ala  Lys
```

```
                                                                        1800
AAG CAA CCA TCC CTT GAG CAA AAT CGC CCA TGG TAA ATT CCA CTA TGG CGA TGG CAT
TTC GTT GGT AGG GAA CTC GTT GAA CTC GGT GGT ACC ATG GGT GAT ACC GCT ACC GTA
Phe Val Gly Arg Leu Glu Val Leu Val Ala Gly Ile Thr Met Gly Asp Thr Ala Thr Val
                                                                        1860
GGA GCG AAT GAC ATG CTA CTT GAA CTT TCG GAC TTG AAT CAT CGC GTT CCG GTT CCA
CCT CGC TTA CTG TAC GAT GAA CTT GAA AGC CTG AAC TTA GTA GCG CAA GGC CAA GGT
Pro Arg Leu Tyr Asp Glu Leu Glu Leu Ser Asn Leu Asn His Val Ala Gln Gly Gln Gly
                                                                        1920
GAA AAT GCG CTT CTG AAC GTT GAG AAG TGT GGG ATG CCT ACT CGG TTA GCA GGC CTA AAT
CTT TTA CGC GAA GAC TTG CAA CTC ACA CCC TAC GGA TGA GCC AAT CGT CCG GAT TTA
Leu Leu Arg Glu Asp Leu Gln Leu Phe Thr Pro Tyr Gly Trp Ala Asn Arg Pro Asp Leu
                                                                        1980
GGT CCC CGA ACT TCA TCA TCA GTG TTG CGT GGG ATG ATG AAG GTG
CCA GGG GCT TGA AGT AGT AGT AGT CAC AAC GCA CCC TAC TTC CAC
Pro Gly Ala Trp Ser Ser Ser Ser His Asn Ala Pro Tyr Tyr Phe His
                                                                        2040
TTA TAG CCC CTA ACT GTT CTG GCA GGT TAG CAA CTA CGG AAA TAA TTC GGG
AAT ATC GGG GAT TGA CAA GAC CGT CCA ATC GTT GAT GCC TTT ATT AAG CCC
Asn Asn Pro Asp Trp Gln Asp Arg Pro Ile Gln Asn Val Val Asp Ala Phe Ile Lys Pro
                                                                        2070                                2100
ACT CTC CTG TTC TTG CCA CTA CGG TTT ATG TAG ATG GGA ATG TCA CCG
TGA GAG GAC AAG AAC GGT GAT GCC AAA TAC ATC TAC CCT TAC AGT GGC
Trp Glu Asp Lys Asn Gly Lys Asp Ala Lys Tyr Ile Tyr Pro Tyr Arg Tyr Ser Gly
```

FIG. 6F

```
                                      2130                                                    2160
TAC ACT CGA ACT GTC CAT ATG TTG ACC AGG TTA TTC GAG TGA CTG GTT AAT TCA CGA
ATG TGA GCT TGA TAC GTA CAG TAC AAC TGG TCC AAT AAG AAG CTC GAC CAA CCA TTA AGT GCT
Met Trp Ala Trp Ala Tyr Gln Val Tyr Asn Trp Ser Asn Lys Leu Thr Asp Gln Pro Leu Ser Ala 2190                                                    2220
CTG AAA CAG TTA CTC TTA CGA ATG GTT GGT TTG AGG AAC AAA CGA TAA GAG TTA GGC
GAC TTT GTC AAT GAG AAT GCT TAC TAC CAA CCA AAC TCC AAC TTT GCT CTC ATT AAT CCG
Asp Phe Val Asn Glu Asn Ala Tyr Gln Pro Asn Ser Leu Phe Ala Ile Leu Asn Pro 2250                                                    2280
CTT AAC AAT CGT CGA GAA GGG CTG TTC CAA TTT ATG CCA TTC CTT TGT CTC AAA CGA CGA
GAA TTG TTA GCA GCT CTT CCC GAC AAG GTT AAA TAC AAG GGT AAG GAA TTT GCT GCT
Glu Leu Leu Ala Ala Leu Pro Asp Lys Val Lys Tyr Gly Lys Glu Phe Ala Ala 2310                                                    2340
TTG CTC ATG CTC GCG AAA TTG GTC TTC AAT TGC CAT CGA GGA TGG GTT CCT TGT TTG ACT
AAC GAG TAC GAG CGC TTT AAC ACG CAG AAG TTA ACG GCT CCT ACC CAA GGA ACA AAC TGA
Asn Glu Tyr Glu Arg Phe Asn Thr Gln Lys Leu Thr Val Ala Pro Thr Gln Gly Thr Asn Trp 2370                                                    2400
AGG GTG AAG AGG GGG TGC GAA AGG GCA AAG TGG CCC AAG TTG GAA CAC CCC AGC CAC
TCC CAC TTC TCC CCC ACG CTT CGT TCC TTC ACC GGG TTC AAC CTT GTG GGG TCG GTG
Ser His Phe Ser Pro Thr Leu Ser Arg Phe Thr Gly Phe Asn Leu Val Gly Ser Val 2430                                                    2460
GAG CTG GTC CAC AAC CTA ATA CAC GGG ACC TAA CCC ATG TCC ATA CCG TTA TTG
CTC GAC CAG GTG TTG GAT TAT GTG CCC TGG ATT GGG AAT GGG TAC AGG TAT GGC AAT AAC
Leu Asp Gln Val Leu Asp Tyr Val Pro Trp Ile Gly Asn Gly Tyr Arg Tyr Gly Asn Asn
```

FIG. 6G

FIG.6H

```
        2490                                              2520
GTG GCC CCG CAC CTA CTA TAT TGG CGC CCC AGC AGG TCG CCT TAA
His Arg Gly Val Asp Asp Ile Thr Ser Ala Gly Ser Ser Gly Ile 2550                                              2580
TCA TGC TTG TGT TCA CCA AGC GCA AGG GGC TGC AAA GAG TTG TAG CCG CAG CCG
AGT ACG ACA AGT GGT TCG CGT TCC CGT TTT CTC CCG TCC AAC ATC GGC GTC GGC
Ser Thr Asn Thr Ser Gly Ser Arg Ser Phe Leu Pro Thr Phe Ser Asn Ile Gly Val Gly 2610                                              2640
GAG TTT CGC TTA CAG GTT CGG TGG GAG CCC CCG TCA GTC TGC TGT CCG CCA AGC
CTC AAA GCG AAT GTC CAA GCC CAA GCC CTC GGG GGC AGT CAG ACA GGC GGT TCG
Leu Lys Ala Asn Val Gln Ala Gln Ala Leu Gly Gly Ser Gln Thr Thr Ile Gly Gly Ser 2670                                              2700
GGA GCT TCT TGG GAG CTG GTT CGG TTC AGT TCA CTG GAG ACT TGC CCC CCC ACT TCC TTA
CCT CGA AGA ACC CTC GAC GCC CAA GTC AGT GAC CTC TGA ACG CGC GGG GGG TGA AGG AAT
Pro Arg Arg Thr Leu Asp Ala Gln Val Ser Asp Leu Trp Thr Gly Ala Gly Trp Arg Asn 2730                                              2760
CTA TTC CGA AGT TCA CCT GTT CAA CTG CTT TTG GTG TGG TTC AAG TGC TCG CGA TGC CCC
GAT AAG GCT TCA AGT GGA CAA GAA GAC GAA AAC CAC ACC AAG TTC ACG AGC GCT ACG GGG
Asp Lys Ala Ser Ser Gly Gln Ser Asp Glu Asn His Thr Lys Phe Thr Ser Ala Thr Gly 2790                                              2820
TAC CTG GTC CCT GTT AGT CCA TGG AGG CGC CCC TTA GGG CTG AGC AAT TTC GTC CTA
ATG GAC CAG GGA CAA TCA GGT ACC TCC GCG GGG AAT CCC GAC TCG TTA AAG CAG GAT
Met Asp Gln Gly Gln Ser Gly Thr Ser Ala Gly Asn Pro Asp Ser Leu Lys Gln Asp
```

```
                                                              3570                                    3600
CCC CAC ACC CGC CTA GTT CGA GTC CAG AGC GTT CCT AGA TGG TGG ACC TGT TCC
GGG GTG TGG GCG GAT CAA GCT CAG GTC TCG CAA GGA TCT ACC ACC TGG ACA AGG
Gly Val Trp Ala Asp Gln Ala Ser Asp Ser Gln Gly Ser Thr Thr Thr Ala Arg 3630                                    3660
TTG CGG AAT GGC CTC GTG CAC CAC TCA AAA CGG AAC GTC CAC CAC CTT CGC TCA
AAC GCC TTA CCG GAG CAC GTG GTG AGT TTT GCC TTG CAG GTG GTG GAA GCG AGT
Asn Ala Leu Pro Glu His Val Val Ser Phe Ala Leu Gln Val Val Glu Ala Ser 3690                                    3720
CGA ATG TTC GGT TTG TGC TCG AGG CCG GTT AGG TGA TTG TCA AGG GGG ATG GAC
GCT TAC AAG CCA CAC ACG AGC TCC GGC CAA TCC ACT AAC AGT TCC CCC TAC CTG
Ala Tyr Lys Pro His Thr Ser Arg Gly Gln Ser Thr Asn Ser Ser Pro Tyr Leu 3750                                    3780
GTG AAC CAC TTC GGA TTC TTT CAA TGG GTT AGG CTG TTC AAT CTG CTA GAA TTT
CAC TTG GTG AAG CCT AAG AAA GTT ACC CAA TCC GAC AAG TTA GAC GAT CTT AAA
His Leu Val Lys Pro Lys Lys Val Thr Gln Ser Asp Lys Leu Asp Asp Leu Lys 3810                                    3840
GAC AAC CTG GGG TTC CAA GCG GTT TCG AAA CCA TGT CTG GTA AGG
CTG TTG GAC CCC AAG GTT CGC CAA AGC TTT GGT ACA GAC CAT TCC
Leu Leu Asp Pro Asn Gln Ser Arg Lys Phe Gly Thr Asp His Ser 3870                                    3900
TGG GTC GGG GTT AGC GAG TTT TGT TGC CAT AAA CCC TGC TCA CCA
ACC CAG CCC CAA TCG CTC AAA ACA ACG GTA TTT GGG ACG AGT GGT
Thr Gln Pro Gln Ser Leu Lys Thr Thr Pro Val Phe Gly Thr Ser Ser Gly
```

FIG. 6K

```
TTG GAG TCA TCA CAC GAA TCA CCA CCC CGA CCT CCA AGA AGT CCA GTT
AAC CTC AGT AGT GTG CTT AGT GGT GGG GCT GGA GGG TCT TCA GGC CAA
Asn Leu Ser Ser Val Leu Ser Gly Ala Gly Gly Ser Ser Gly Gln      3960
                                                   3930

AGA CCG CAC CTA GAG AGG GGG CAA CTT TTT CAC CCC ACC GAA CAC CCC AAT GGT
TCT GGC GTG GAT CTC TCC CCC GTT GAA AAA GTG TGG GGG CTT GTG CAG TTA CCA
Ser Gly Val Asp Leu Ser Pro Val Glu Lys Val Trp Gly Leu Val Gly Gln Leu Pro
                            3990                                      4020

TCG TGC TCA CTG CCT TTG TGG AGG TCC CGA TTA GAG CGG GGA TTA TGA TGC CCC
AGC AGT GAC GGA AAC ACC TCC AGG GCT CTC GCC CCT AAT ACT AAT ACG GGG
Ser Ser Asp Gly Asn Thr Ser Ser Arg Ala Leu Ala Pro Asn Thr Asn Thr Gly
         4050                                                    4080

TTA CAC CAC CCC CAA CCA GCT GAA AGA CTT TCG TTG CGG TTC TAC CTG CTA
AAT GAT GTG GGG GTT GGT CGA CTT TCT AAC AGC GCA AAG ATG GAC GAT
Asn Asp Val Val Gly Val Gly Arg Leu Ser Glu Ser Asn Ala Ala Lys Met Asn Asp Asp
                          4110                                           4140

CAA CTA CCA TAA CAT GCG TGG GGT GAG CGA CTT GAC AAT CTA CCC CTT CCT TGT CGA
GTT GAT GGT ATT GTA CGC ACC CCA CTC TCT GAC CTG TTA GAT GGG GAA CAA ACA GCT
Val Asp Gly Ile Val Arg Thr Pro Leu Ala Glu Leu Leu Asp Gly Glu Gln Thr Ala
                        4170                                         4200

CTG TGA CCA GGT GTT TCG CAC TTC AAG AGA GGA CTG GTT TAA ATT GAC TTC AAC TTG
GAC ACT GGT CCA CAA AGC GTG AAG TCT CCT GAC CAA CAA ATT GAC TTC AAC GCG
Asp Thr Gly Pro Gln Ser Val Lys Phe Lys Ser Pro Asp Leu Val Gln Ile Asp Phe Asn Arg Leu
                4230                                            4260
```

FIG.6L

```
                                                                    4320
AAA TGG GTG GGT CAG TGG CTA GAC AAA TTT GAC CTA GGC CAT TGA TAC AAC CAC ATA CTG GTC
TTT ACC CAC CCA GTC ACC GAT CTG TTT GAT CCG GTA ACT ATG GTG TAT GAC CAG TAC
Phe Thr His Pro Val Thr Asp Leu Phe Asp Pro Val Thr Met Leu Val Tyr Asp Gln Tyr
                              4290                                                  4380
TAT GGC GAC AAA TAA CTA TAG GGT CGT TCA CAC TTG GGA TTT CAA GCT AAT TTC CAG
ATA CCG CTG TTT ATT GAT ATC CCA AGT GCA GTT AAC CCT AAA ATG GTT CGT TTA AAG GTC
Ile Pro Leu Phe Ile Asp Ile Pro Ala Ser Val Gly Met Val Arg Leu Lys Val
                              4350                                                  4440
AAC TCG AAA CTG TGG CTT GTC TCG AAT CCA GAG GCG AAT CTC AAG AAA TTT GGA CTA
TTG AGC TTT GAC ATC GAA CAG AGC TTA GGT CTC CGC TTA GAG TTC AAA CCT GAT
Leu Ser Phe Asp Thr Asn Glu Ser Leu Arg Leu Gly Leu Glu Phe Lys Pro Asp
                              4410                                                  4500
GTT CTA TGG GTT GGT TTG CAA GTC CAG TTA GGC TTA TTG CCA AAG AAT GGT
CAA GAT ACC CAA GTT AAC AAC GTT CAG CCG AAT AAC GGT GAC TTC TTA CCA
Gln Asp Thr Gln Pro Asn Asn Val Gln Pro Asn Asn Gly Asp Phe Leu Pro
                              4470                                                  4560
GAC AAT TGC CGG AGG TCA GTT CCA GGG GTT CCA CAA GGT CCC CAA GGT TGG AAC AAA TCA GGC AAA TTG GTC ACT GGA
CTG TTA ACG GCC TCC AGT CAA GGT CCC CAA GGT CAG CCG TTT AAC CAG TGA CCT
Leu Thr Ala Ser Gln Pro Gly Pro Phe Ser Pro Phe Asn Gln Trp Pro
                              4530                                                  4620
CTA ATG CAC AAC GGC AAT CGC TAG TGA CAT GGA TAA CAA CAC GAG TCA CAA TGG
GAT TAC GTG TTA CCG ATC GCG TTA ACT GTA CCT ATT GTT GTG CTC AGT GTT ACC
Asp Tyr Val Leu Pro Leu Ala Ile Thr Val Pro Ile Val Val Leu Ser Val Thr
                              4590

FIG.6M
```

FIG.6N

METHODS AND COMPOSITIONS FOR PRODUCTION OF MYCOPLASMAL ADHESINS

The Government may own certain rights in this invention pursuant to National Institute of Health, Grant Number AI 18540, awarded by the Department of Health & Human Sciences.

This application is related to co-pending U.S. application Ser. No. 07/004/767, which is incorporated herein by reference.

BACKGROUND OF THE INVENTION

1. FIELD OF THE INVENTION

This invention relates to the molecular cloning of the gene encoding *Mycoplasma pneumoniae* P1 cytadhesin protein. This protein mediates mycoplasmal colonization of host respiratory epithelium and is a critical virulence determinant. By the present invention, a complete DNA sequence of the complete P1 gene as well as a deduced amino acid sequence of the P1 cytadhesin protein is presented for the first time. In addition, clones expressing *M. pneumoniae* peptides are provided. Those peptides contain the functional cytadhesin epitopes and have been used to localize the cytadhesin binding domain of P1.

2. DESCRIPTION OF THE RELATED ART

*M. pneumoniae* is a non-invasive pathogen that colonizes the mucosal surface of the respiratory tract and causes a primary, atypical pneumonia. Although this disease appears to occur most frequently in young adults and children, its incidence in the general population may be underestimated because the symptoms are often relatively mild and diagnostic procedures are suboptimal.

*M. pneumoniae* initiates infection by colonizing cells of the respiratory epithelium. This colonization is mediated by a specialized tip-like organnelle containing clusters of a surface-localized, trypsin sensitive protein designated P1. Numerous studies show P1 to be a critical virulence determinant. For example, mutants of *M. pneumoniae* that lack P1 or are unable to mobilize and anchor P1 at the tip are avirulent. In addition, treatment of virulent *M. pneumoniae* with trypsin abrogates adherence to the respiratory epithelium. Finally, monoclonal antibodies to P1 have been shown to block *M. pneumoniae* cytadherence. Plummer, et al., *Infect. Immun.*, 53:398–403 (1986).

Unfortunately, despite the critical importance of P1 as a mycoplasmal virulence determinant, efforts to provide a cloned gene encoding the P1 cytadhesin have been generally unsatisfactory. For example, Trevino, et al., *Infect. Immun.*, 53:129–134 (1986), describe an attempt to clone *M. pneumoniae* antigens by constructing an *M. pneumoniae* genomic library using lambda phage EMBL3 as the vector and immunoscreening the library with adsorbed anti-*M. pneumoniae* serum. Although this procedure produced several clones exhibiting antigenic cross-reactivity with *M. pneumoniae* P1, none of the clones reacted with monoclonal antibodies specific for critical antigenic determinants of P1 shown by the present inventors to mediate cytadherence. Moreover, the largest immunoreactive protein identified had a molecular weight of only 140 kDa. In contrast, native P1 has a molecular weight of approximately 165 kDa. Therefore, it could not be definitely established whether or not the 140 kDa protein was a product of the structural P1 gene. The approach was then abandoned.

Since the P1 cytadhesin is probably the most important mediator of mycoplasma cytadsorption, further elucidation of the structure of this molecule is likely to provide information essential for a complete understanding of the role of cytadherence in pathogenesis of mycoplasmal disease. This goal can be achieved most readily by cloning and sequencing the structural gene encoding P1. Furthermore, recent studies have shown that adherence of mycoplasma to respiratory epithelium can be inhibited by certain antibodies directed against cytadhesin epitopes of P1. Therefore, vaccines comprising recombinant P1 protein or selected cytadhesin polypeptides derived from recombinant P1 are likely to prove effective in preventing mycoplasmal infection. In addition, the availability of the complete gene sequence and deduced amino acid sequence for *M. pneumoniae* P1 will allow one to map critical antigenic epitopes and produce selected synthetic peptides useful as diagnostic probes or vaccines.

SUMMARY OF THE INVENTION

By the present invention, the cloning and DNA sequencing of the complete P1 gene is described for the first time. In addition, the complete amino sequence of the P1 protein is provided. The invention also provides recombinant P1 polypeptides, including polypeptides expressed as fusion proteins comprising cytadhesin epitopes. Accordingly, in a general and overall scope, the present invention comprises recombinant clones encoding P1, recombinant DNA sequences suitable for use as hybridization probes to assist cloning of genes encoding P1 and other mycoplasmal cytadhesins, methods for isolating such genes, and recombinant P1 polypeptides.

More particularly, the invention relates to substantially purified nucleic acid molecules comprising a nucleotide sequence encoding the P1 protein or portion of the C-terminal portion thereof. Of course, absolute purification of the nucleic acid molecule is not necessary. Rather, the term "substantially purified" is intended to distinguish the claimed species from species found in nature. Moreover, it will be appreciated that there is no requirement that the nucleic acid encode a complete P1 protein. All that is required is that the molecule encode at least a portion of the C-terminal portion of the P1 protein. For the purposes of the present invention, a C-terminal portion of P1 is defined as the portion of P1 encoded by nucleotides downstream from nucleotide 2440.

In a further embodiment, the substantially purified nucleic acid molecule encodes a P1 protein having molecular weight of about 165-170 kDa. In yet still a further embodiment, the invention relates to a nucleic acid molecule wherein the nucleotide sequence is defined as a nucleotide sequence encoding the amino acid sequence of FIG. 6. Although the term nucleic acid is meant to include both ribonucleic acid (RNA) and deoxyribonucleic acid (DNA), DNA is preferred for the purposes of the present invention. Accordingly, in one embodiment, the nucleic acid is described as DNA.

In addition, the invention provides a substantially purified nucleic acid molecule comprising a nucleotide sequence encoding an *M. pneumoniae* P1 polypeptide having a cytadhesin epitope. For purposes of the present invention, a polypeptide is defined as a peptide of more than one amino acid, and a P1 cytadhesin epitope is considered to be any P1 polypeptide which binds to an antibody capable of inhibiting P1 mediated cytadherence or is itself capable of competitively inhibiting P1 mediated cytadherence. For example, a more specific embodiment relates to a nucleic acid molecule wherein the cytadhesin epitope encoded is capable of reacting immunologically with monoclonal antibody 5B8, produced by ATCC #HB9586. Similarly, an additional embodiment is directed toward a nucleic acid molecule where the cytadhesin peptide is capable of reacting immunologically with monoclonal antibody 6E7, produced by ATCC #HB 8420. Further embodiments of the invention relate to nucleic acid molecules comprising DNA sequences encoding *M. pneumoniae* P1 polypeptides of at least thirteen amino acids in length. More specifically, the invention provides for nucleic acid molecules wherein the P1 polypeptide comprises at least the particular amino acid sequence of the thirteen amino acid cytadhesin epitope described by the present inventors, or the amino acid sequences corresponding to those expressed by phage clones P1-7, P1-9, and P1-10. These amino acid sequences are described by claims 8, 9, 10, and 11, respectively.

Of course, as those of skill in the art will appreciate, the DNA sequences claimed are not required to be actively expressing mycoplasmal P1 polypeptides or in a proper expression vector or expression frame to express the polypeptide. In addition, due to the redundancy of the genetic code, a number of nucleotide sequences may encode the indicated amino acid sequences. Any such nucleotide sequence is considered to be within the scope of the present invention. Moreover, those of skill in the art will appreciate that, in some cases, conservative amino acid substitutions may allow the production of a polypeptide which has a slightly different amino acid sequence than any of those recited in the claims, but has essentially identical function. Such polypeptides are considered to be functional equivalents of the polypeptides described herein and nucleotide sequences encoding such polypeptides are considered to be within the scope of the present claims.

Additional embodiments of the invention are directed towards DNA vectors comprising any one of the DNA molecules described above as well as toward bacterial strains comprising such recombinant vectors. In a more particular embodiment, the bacterial strain is defined as *E. coli*.

A further embodiment of the invention is directed towards DNA molecules comprising a DNA sequence which includes at least a tetradecameric portion of the DNA sequence of FIG. 6. These DNA molecules are believed to possess a number of utilities. First, they may be used as hybridization probes to assist in cloning the P1 gene from *M. pneumoniae*. In addition, it is contemplated that they may be used to detect homologous nucleotide sequences in other mycoplasmal species, and thus aid in cloning of cytadhesin genes from such species, *M. genitalium*, for example. Of course, in some cases they may also be used to direct synthesis of the polypeptides encoded.

In more specific embodiments of this aspect of the invention, particular nucleotides sequences are claimed. For example, embodiments directed to DNA molecules wherein the DNA sequence comprises nucleotides 178 to 191 or 196 to 213 of FIG. 6 are essentially directed to the 14-mer and 18-mer probes encoding the amino acids shown in FIG. 2A or 2B, respectively. A further embodiment, directed towards the DNA sequence comprising nucleotides −70 to 258 of the DNA sequence of FIG. 6 is essentially directed towards the nucleotide sequence of the Hae III restriction fragment described herein. A still further embodiment is directed to the EcoRI/Pst I restriction fragment (nucleotides −204 to 911) used by the present inventors to isolate the P1 gene. Of course, yet another embodiment is directed to the DNA fragment containing the complete structural gene itself. Additional embodiments are directed to the DNA molecule encoding the thirteen amino acid cytadhesin epitope (nucleotides 4148–4185) and to DNA sequences comprising the DNA inserts of phage clones P1-7 (nucleotides 4067–4085), P1-9 (nucleotides 4148–4881), and P1-10 (nucleotides 4202–4881), respectively. Yet still a further embodiment is directed to a DNA sequence comprising at least the transcribed portion of the DNA sequence of FIG. 6. Yet still a further embodiment is directed to the DNA sequence of FIG. 6.

It will be readily apparent to those skilled in the art that FIG. 6 depicts both the coding and non-coding strand of the P1 DNA. It should be expressly pointed out that the claims of the present invention are not limited to double stranded DNA molecules, but are intended to encompass both double stranded and single stranded molecules, since, in many systems, either strand may be used as a nucleotide probe and one strand may easily be produced from its complementary strand. The only requirement is that the DNA molecule include the specified nucleotide sequence.

In addition, although certain embodiments refer only to DNA molecules, those of skill in the art will also appreciate that the DNA sequences of the present invention can easily be transcribed into a corresponding RNA molecule. Therefore, RNA molecules corresponding to the DNA sequences of the present invention are considered to be functional equivalents of such DNA molecules and are intended to be encompassed by the present claims.

Additional embodiments of the invention relate to DNA molecules capable of hybridizing to the recombinant insert of the 6 kbp EcoRI fragment designated plasmid pMPN P1 under selected hybridization conditions, said molecules suitable for use as hybridization probes. For example, one embodiment is directed toward a DNA molecule capable of hybridizing to the recombinant insert of plasmid pMPN P1, obtainable from ATCC #67560 (pending) under moderately stringent hybridization conditions while another embodiment is directed toward a DNA molecule capable of hybridizing to the recombinant insert of plasmid pMPN P1, obtainable from ATCC #67560 under stringent hybridization conditions. For the purposes of the present invention, such conditions are described as moderately stringent in that they allow detection of a nucleotide sequence at least 14 nucleotides in length having at least approximately 75% homology with the sequence of the nucleotide probe used. Stringent hybridization conditions are defined as conditions wherein the probe detects nucleotide sequences at least 14 nucleotides in length having a homology greater than about 90%. The conditions necessary for hybridization of a particular probe to a particular nucleotide sequence having a specified degree of homology may be determined by referring to *Nucleic Acid Hybridization, A Practical Approach*, Hames and Higgins, eds., IRL Press, Oxford and Washington, 1985, or Wood, et al., PNAS, 82:1585–1588 (1985), both incorporated herein by reference.

In addition, claims are directed toward recombinant DNA vectors comprising the claimed DNA molecules as well as bacterial cells comprising such recombinant vectors. In a more particular embodiment, the bacterial cells are defined as *E. coli.*

The invention also includes polypeptide fragments of *M. pneumoniae* having *M. pneumoniae* P1 cytadhesin epitopes. More specific embodiments are directed toward polypeptides further defined as being capable of immunospecifically binding to monoclonal antibody 6E7, ATCC #HB 8420. Similarly, an additional specific embodiment is directed towards polypeptides defined as capable of immunospecifically binding to monoclonal antibody 5B8, ATCC #HB 9586. Of course, where the recombinant polypeptide is encoded by a DNA sequence inserted in a particular type of expression vector, the polypeptide will be expressed as a fusion protein. For example, when lambda gt11 is used as an expression vector, the *M. pneumoniae* polypeptide will be expressed in the form of a beta-galactosidase fusion protein. Although such fusion proteins are considered to be polypeptides and, thus, intended to be encompassed by the claims of the present invention, one embodiment is specifically directed to fusion proteins.

Additional claims are directed towards polypeptides comprising specific sequences as outlined in the claims. Of course, recombinant polypeptides are included within the scope of the present invention. Moreover, synthetic polypeptides can be prepared from known amino acid sequences. The present invention is also meant to encompass any synthetic polypeptide comprising the claimed amino acid sequences or polypeptides having conservative amino acid substitutions and essentially identical function. Additional embodiments of the invention relate to vaccines comprising such polypeptides and methods for inducing resistance to *M. pneumoniae* infection. Still further embodiments relate to diagnostic kits comprising polypeptides having cytadhesin epitopes.

More specifically, the invention provides for a cytadhesin polypeptide corresponding biologically to that produced by clones P1-7, P1-9 or P1-10, ATCC #40386, 40385 or 40384 respectively. For the purposes of the present invention, a cytadhesin polypeptide corresponding biologically to a polypeptide encoded by an identified recombinant vector is considered to be any polypeptide having similar or identical function to that encoded by the specified recombinant vector. Such peptides may include synthetic peptides, including synthetic peptides having a slightly different amino acid sequence but essentially similar function. In a more specific embodiment, the polypeptides are further defined as *M. pneumoniae* P1 polypeptides.

With even more particularity, the invention provides for a number of DNA molecules comprising a recombinant DNA vector which includes the recombinant inserts of phages P1-7, P1-9, P1-10, ATCC #40386, ATTC #40385, ATCC #40384, respectively. The invention also includes a recombinant DNA vector which includes a recombinant insert of plasmid pMPN P1, ATCC #67560 (pending). Bacterial strains comprising recombinant vectors which include such inserts are also included.

Finally, yet another feature of the present invention relates to a method for screening mycoplasmal DNA for DNA sequences that correspond to those of *M. pneumoniae* P1, using the novel nucleotide sequences of the present invention. This method essentially comprises fractionating mycoplasmal DNA to produce DNA fragments; separating the DNA fragments according to their sizes or molecular weights; hybridizing the DNA fragments with DNA molecules provided by the present invention; and identifying at least one fragment which hybridizes to said DNA molecules by means of a label.

Of course, the method will prove useful for isolation of *M. pneumoniae* DNA sequences. However, it may also be useful for screening other Mycoplasmal species for homologous genes encoding *M. pneumoniae* P1. For example, the present inventors have observed that portions of the *M. pneumoniae* P1 gene are homologous to a gene from *M. genitalium.* Therefore, one embodiment of the present invention relates to screening of *M. genitalium.* The specificity of the novel nucleotides probes will depend, in part, on the hybridization conditions used. For example, where one desires to isolate nucleotide sequences encoding proteins homologous but not identical to *M. pneumoniae* P1, less stringent hybridization conditions should be used.

Methods which have proved particularly useful in fragmenting the DNA utilize restriction enzyme digestion or mechanical shearing. However, restriction enzyme digestion was utilized for the practice of the present invention. More particularly, the invention provides for digestion of the mycoplasmal DNA with the restriction enzyme EcoRI.

The fragmented DNA can be separated into recognizable patterns using various methods, the most useful of which take advantage of the varying sizes of discrete DNA fragments. For example, DNA fragments can be separated according to molecular weight by velocity sedimentation through a density gradient or, by molecular size exclusion chromatography. However, for purposes of the present invention, the preferred technique is to separate the DNA fragments by electrophoresis through an agarose or polyacrylamide gel matrix.

The P1 hybridization probe can be conveniently labeled with radioactive nucleotides which allow for ready visualization of the hybridized DNA by autoradiography. Of course, other labeling techniques, including heavy isotopes or biotinylation, may also be used.

It should also be appreciated there is also no absolute requirement that the hybridization probes be derived from cloned *M. pneumoniae* P1 DNA. Since the present invention provides the complete gene sequence of *M. pneumoniae* P1, various oligonucleotide probes can be synthetically prepared on the basis of the disclosed sequence.

The substantially purified DNA molecules, recombinant DNA cloning vectors, recombinant cells, and recombinant proteins of the present invention may be used to prepare *M. pneumoniae* P1 polypeptide fragments or fusion proteins suitable for use as vaccines or reagents for use in diagnostic kits. Furthermore, the substantially purified DNA sequences of the present invention are likely to prove useful as hybridization probes for selectively isolating mycoplasmal cytadhesin genes. Modification of the products of the present invention so as to facilitate their utility in these or other areas is considered to be well within its scope.

CHARACTERISTICS OF DEPOSITED MICROORGANISMS

Recombinant lambda gt11 vectors P1-7, P1-9, and P1-10 comprising clones P1-7, P1-9, and P1-10 have been deposited under the Budapest Treaty with the American Type Culture Collection, Rockville, Md., and assigned ATCC accession numbers 40386, 40385, and 40386, respectively. These clones comprise lambda gt11 bacteriophages having a mycoplasmal DNA sequence ligated into the EcoRI site within the beta-galactosidase gene.

E. coli HB101 comprising a recombinant pUC 19 plasmid vector having a mycoplasmal DNA insert approximately 6 kbp in length ligated into the EcoRI site (plasmid pMPN P1) has been deposited under the Budapest Treaty with the American Type Culture Collection, Rockville, Md., and assigned ATCC accession #67560.

BRIEF DESCRIPTION OF THE DRAWINGS

FIG. 1—SDS-polyacrylamide gel electrophoresis analysis of protein samples during the purification of P1.

FIG. 1 (A) total protein extract from *M. pneumoniae.* Arrow indicates the position of P1;

FIG. 1 (B) same sample from FIG. 1 (A) after a single passage through the anti-P1 affinity column;

FIG. 1 (C) protein eluted from the anti-P1 affinity column; and

FIG. 1 (D) P1 after preparative gel electrophoresis and electroelution. Proteins were separated by 7.5% polyacrylamide gel electrophoresis and stained with Coomassie blue.

FIG. 2—The N-terminal 18 amino acid sequence of protein P1 and the 14-mer and 18-mer oligonucleotide probes designed to hybridize to the P1 gene. The 14-mer covers amino acids 1 to 5 and the 18-mer covers amino acids 7 to 12. X=ACGT.

FIG. 3—*M. pneumoniae* DNA (12 ug/lane) digested with different restriction enzymes and separated by 0.7% agarose gel electrophoresis.

FIG. 3 (A) standard;

FIG. 3 (B) EcoRI;

FIG. 3 (C) Hae III;

FIG. 3 (D) Pst I;

FIG. 3 (E) Hind III;

FIG. 3 (F) BamHI;

FIG. 3 (G) Kpn I; and

FIG. 3 (H) Sal I.

FIG. 4—Southern blot analysis of *M. pneumoniae* genome. *M. pneumoniae* DNA was digested with Hind III, separated by 0.7% agarose electrophoresis and transferred to nitrocellulose paper according to the method of Southern (Mizusawa, et al., *Nucleic Acids Res.,* 14:1319–1324 (1986)). The nitrocellulose strip was then hybridized to the 14-mer (A) and 18-mer (B) probes labeled with $^{32}P$. A single band (4.3 kb) hybridizes to both probes (arrow).

FIG. 5—Restriction enzyme map of the P1 gene. The first clone (62A) contains the 4.3 kb Hind III piece, and the second clone contains the 6 kb EcoRI piece. Both the 14-mer and 18-mer probes hybridize to the DNA at a site very close to the first Sma I site. The cross-hatched box represents the P1 structural gene.

FIG. 6A–N—Complete nucleotide sequence and deduced amino acid sequence of the P1 gene. Both the coding and non-coding strand is shown. The presumed starting codon of P1 (ATG) is numbered as 1. In the 5′ flanking region, the possible promoter elements (−10 and −35) are underlined. The 18 amino acids which match those determined by protein sequencing of P1 are boxed (nucleotides 178–231). In the 3′ flanking region, a sequence with dyad symmetry, which may be a termination signal, is indicated by the arrows and the "*" indicates mismatched sequences in this sequence. The complete P1 gene contains 4881 nucleotides coding for a protein of a calculated 176,288 daltons which includes an apparent leader peptide (see text).

FIG. 7—Plot of hydrophilicity value versus sequence position of P1 according to the method of Hopp and Woods, *Proc. Natl. Acad. Sci., U.S.A.,* 78:3824–3828 (1981). Hydrophilicity values are averaged over six amino acids through the length of P1; highest positive values represent charged hydrophilic regions.

FIG. 8—Location of the ten lambda gt11 clones within the P1 structural gene. The predicted fusion protein size and DNA insert size of each clone are given. Molecular weight values of the *M. pneumoniae* fusion proteins were calculated by subtracting the value of the beta-galactosidase protein (116 kD). ⌊__⌋ indicates the location and dimension of the insert size. The numbers indicate nucleotides encompassed by each clone. A "t" indicates that the clone extends through the end of the P1 gene. As indicated in text, a TGA stop codon exists just downstream from the EV site.

FIG. 9A–B—Gene sequence and deduced protein sequence of epitopes involved in cytadherence by *M. pneumoniae.* The 13 amino acids within which one epitope is located are underlined. Symbols corresponds to the following : ▼, start of clone P1-7; ▲, end of clone P1-7; *, start of clone P1-9; and ∇, start of clone P1-10. The stop codon is indicated by the box.

FIG. 10—Hybridization of $^{32}P$-labeled *M. pneumoniae* insert DNA from clone P1-7 to *M. pneumoniae* genomic DNA digested with EcoRI (lane A), Hind III (lane B), Pst I (lane C), Sac I (land E), and Sma I (lane E). Molecular weights in kb are shown at the left.

FIG. 11—Immunoblot of cytadhesin fusion proteins using anti-P1 MAbs. Lane A represents total *M. pneumoniae* proteins reacted with a pool of the two MAbs designated 5B8 and 6E7 (see text). Lane B is the beta-galactosidase protein reacted with a monoclonal Ab to beta-galactosidase (Promega Biolab, Madison, Wis.). Lanes C and D are clones P1-7 and P1-9, respectively, reacted with MAb6E7. Lane E is clone P1-10 reacted with MAb5B8.

FIG. 12—Immunophage blot of the ten different clones reacted with acute (I) and convalescent (II,III) sera of patients infected with *M. pneumoniae.* Numbers 7, 9, and 10 indicate clones P1-7, P1-9, and P1-10, respectively.

DETAILED DESCRIPTION OF THE PREFERRED EMBODIMENTS

The present invention describes the isolation and nucleic acid sequence of the gene encoding the P1 cytadhesin protein from *M. pneumoniae,* the amino acid sequence of P1, and production of highly antigenic P1 polypeptides, including fusion proteins.

The present invention is disclosed in terms of two general approaches employed by the inventors to isolate clones and identify nucleic acid sequences encoding *M. pneumoniae* P1 protein, or highly antigenic *M. pneumoniae* polypeptides. The first general approach is primarily directed toward isolating, cloning, and sequencing the complete *M. pneumoniae* P1 gene, while the primary goal of the second approach is to identify particular nucleotide sequences encoding the functional cytadhesin domains of P1 and to produce antigenic cytadhesin polypeptides suitable for use as diagnostic reagents or vaccines.

As indicated earlier, past attempts to clone the P1 gene were found to be generally unsatisfactory. This failure was due, at least in part, to lack of a suitable method for unequivocally demonstrating that a particular cloned DNA sequence actually represented the P1 gene. Fortunately, the present inventors have now discovered a technique allowing the complete structural P1 gene to be isolated and cloned. The P1 gene has now been completely sequenced and the nucleotide sequence unequivocally established as the structural P1 gene. In addition, the amino acid sequence of the complete P1 protein has been deduced from the nucleotide sequence.

Accordingly, the general approach described below represents a particularly preferred approach for obtaining recombinant DNA clones containing the complete P1 gene. However, as illustrated below, the method has also been successfully used for cloning partially complete P1 genes.

The technique described below, disclosed for the first time by the present application, is one preferred method for obtaining recombinant DNA molecules and clones of the present invention. Of course, variations of this method may also allow the gene to be cloned successfully. It is also possible that other techniques could be successfully used to clone *M. pneumoniae* P1. Any *M. pneumoniae* P1 gene cloned by such procedures is considered to be within the scope of the present invention, unless the claims provide otherwise.

In general, recombinant clones produced in accordance with the present invention are made by first isolating mycoplasmal DNA. Any mycoplasma encoding the P1 protein, may be used as a source of DNA. However, virulent strains of *M. pneumoniae* are preferred. These strains include, but are not limited to, *M. pneumoniae* isolated from infected humans or animals, as well as defined strains maintained as laboratory cultures. The strain *M. pneumoniae* M129 is particularly preferred.

A number of methods for extracting DNA from prokaryotic organisms are known which may, with possible routine modifications within ordinary skill in the art, be used to extract mycoplasmal DNA. A preferred method generally comprises lysing the organisms in a lysing buffer, for example, sodium dodecyl sulfate in phosphate-buffered saline, extracting the DNA from the lysed cell mixture with a suitable organic solvent such as phenol, n-butanol or chloroform and reprecipitating the DNA with a suitable reagent such as ethanol, ethanol-acetate or isopropanol.

The extracted DNA is then fragmented. Any of a number of techniques suitable for producing DNA fragments, such as mechanical shearing or partial or complete restriction enzyme digestion, may be used. However, where a complete clone of the structural gene is desired, it is important to fragment the DNA so as to produce fragments at least about 4.75–5.0 kb.

In general, digestion with restriction enzymes is a preferred method of fragmenting the mycoplasmal DNA. Although any of a number of restriction enzymes may be used (for example, see those listed in *MOLECULAR CLONING*, Maniatis, et al., Cold Spring Harbor Laboratory, Cold Spring Harbor, N.Y., pp. 93–103) under properly selected digestion conditions, the present inventors have discovered that the *M. pneumoniae* genome contains an EcoRI site on either side of the P1 structural gene, but not within the gene itself. Therefore, when EcoRI is used as a restriction enzyme, complete digestion of *M. pneumoniae* DNA will produce a single DNA fragment containing the entire structural gene. For this reason, it is especially preferred that the *M. pneumoniae* DNA be digested to completion with EcoRI in cases where a full length structural gene is desired.

Conversely, if one desires to obtain a fragment containing only a portion of the P1 structural gene, complete digestion with Sal I, Pst, BamHI, Kpn I, Sma I, Sac I, Hind III, or Eco RV may be used since the P1 structural gene is now shown to contain restriction sites for these enzymes. Of course, it may be also possible to use these enzymes in partial digestion procedures in cases where a full length P1 gene is desired.

The fragmented DNA can be separated into a recognizable pattern using various methods, the most useful of which take advantage of the varying sizes of the discrete DNA fragments. For example, DNA fragments can be separated according to molecular weight by velocity sedimentation through a density gradient, or by molecular size by gel exclusion chromatography. However, according to a technique preferred for the purposes of the present invention, DNA fragments are separated by electrophoresis through an agarose gel matrix and then transferred to a nitrocellulose sheet so that an exact replica of the DNA fragments in the gel is transferred to the nitrocellulose sheet.

A specific labelled probe is then applied to the nitrocellulose sheet under selected hybridization conditions so as to hybridize with complementary DNA fragments localized on the sheet. Although various labels known to those of skill in the art may be employed, a radioactive probe is preferred. The sheet may then be analyzed by autoradiography to locate particular fragments which hybridize to the probe.

Various hybridization probes may be used to detect the P1 structural gene. For example, in experiments performed in conjunction with development of the present invention, the N-terminal amino acid sequence of the P1 protein was determined and two oligonucleotides based on this sequence (the 14-mer and 18-mer probes described in Example I) were utilized. In subsequent experiments, an EcoRI/Pst I restriction fragment digested from an incomplete P1 clone (62A) was used as a hybridization probe. However, as those of skill in the art will appreciate, any number of suitable hybridization probes can now be prepared, based on sequences contained within the complete P1 gene sequence provided for the first time by the present invention. All that is required is that the DNA fragments to be used as probes be of sufficient length to form a stable duplex or hybrid with the P1 DNA. Such fragments are said to be "hybridizable" in that they are capable of stable duplex formation. Generally, a DNA fragment of at least fourteen nucleotides in length (a tetradecamer) is capable of forming a stable duplex. Of course, in practice, it may be sometimes preferable to use a probe containing more nucleotides or alternatively, to use a battery of individual probes to detect a single fragment that hybridizes to each probe in the battery.

In any event, after DNA of the size range containing the desired restriction fragments is identified by the procedure generally described above, the fragment may be removed from the gel by a variety of techniques known to those of ordinary skill in the art (e.g., electroelution, dialysis, etc.) and cloned into an appropriate vector. Although it is likely that the restriction fragment containing the P1 gene could successfully be cloned into several types of vectors, (e.g., cosmids or phage), it is generally preferred to use a plasmid cloning vector, particularly where the desired restriction fragment is smaller than 15 kbp.

After construction of recombinant vectors, the vectors are used to transform an appropriate host. In a preferred embodiment, the host is an *E. coli* cell of a type which is compatible with the selected vector type. However, although the present invention is disclosed in terms of *E. coli* host/vector systems, other host/vector systems are known in the art and may be employed where desired. For example, see those described in *DNA Cloning* (Vol. II), P. M. Glover, ed., IRL Press, Oxford, Washington, D.C. (1985).

Transformation of host cells by the recombined vector is achieved using standard procedures known in the art. For example, where plasmid vectors are employed, transformation is typically achieved by permeabilizing competent cells with calcium and contacting the permeabilized cells with the recombinant vector DNA. Where bacteriophage vectors are employed, one may additionally choose to package the recombinant phage with phage coat proteins, which affords direct transformation capability through cell infection with a resultant increase in transformation efficiency.

Once the cells are successfully transformed with the recombinant vector DNA, they are culture plated to provide individual recombinant clonal colonies or plaques, a portion of which may express proteins or peptides encoded by the *M. pneumoniae* P1 genome. In addition, clones may be used as a source of *M. pneumoniae* DNA suitable for subcloning, sequencing studies or use as hybridization probes.

The second general approach utilized by the present inventors relates to cloning and expression of *M. pneumoniae* DNA encoding polypeptides having a cytadhesin epitope. The polypeptides so produced may be used as diagnostic reagents or vaccines.

The focus of this approach differs somewhat from that described above in that it is generally directed toward isolation and expression of *M. pneumoniae* DNA that encodes a particular functional domain of the P1 protein, the domain responsible for cytadherence. In general then, this second approach involves fragmenting *M. pneumoniae* DNA by procedures similar to those described above and using the fragmented DNA to construct an *M. pneumoniae* DNA library or clone bank which is then screened with a reagent specific for clones encoding cytadhesin epitopes.

The DNA libraries may generally be constructed in either plasmids or bacteriophage, however, where expression of the cloned gene sequence is desired, it is preferred that the library be constructed in an expression vector. The lambda gt11 expression vector is particularly preferred where expression of the cloned gene is desired because use of lambda gt11 has been found to ameliorate several problems generally associated with production of foreign proteins in *E. coli*. (See Huynh, et al., In DNA Cloning (Vol. I), E. M. Glover, ed., IRL Press, Oxford, Washington, D.C. (1985) and incorporated herein by reference.) Of course, it is contemplated that a number of other vectors could also be used to generate and/or express the *M. pneumoniae* DNA library.

The library may be screened for clones containing the DNA sequences encoding the cytadhesin domain of P1 by various procedures so long as the screening reagents used allow isolation of a recombinant DNA clone encoding at least a portion of the cytadhesin domain. For example, the present inventors used monoclonal antibodies previously shown to recognize the cytadhesin binding domain of *M. pneumoniae* P1 (See Morrison-Plummer, et al., *Infect. Immun.*, 55:49–56 (1987)). Notably, those antibodies do not react with the DNA clones described by Trevino, et al.

Of course, since the present disclosure describes the nucleic acid sequence of the critical regions of the P1 gene, nucleic acid hybridization probes that selectively hybridize to these regions of the P1 genome may also be used for screening. (For examples of a nucleic acid screening procedure, see Huynh, et al., In DNA Cloning (Vol. I), E. M. Glover, ed., IRL Press, Oxford, Washington, D.C. (1985)). However, where one desires to screen with specific nucleic acid probes, lambda gt10 may be a preferred vector.

Once clones containing the *M. pneumoniae* cytadhesin epitopes are isolated, they may then be expanded and used as a source of *M. pneumoniae* DNA for sequencing studies. The sequence of the DNA inserts of the selected clones can then be compared with the complete DNA sequence of the P1 gene provided for the first time by the present invention. In this manner, the cloned inserts can be unequivocally identified as encoding all or part of the P1 protein.

DNA or deduced amino acid sequences from a battery of clones may then be correlated with the antigenic phenotype of the polypeptides produced by such clones to precisely map the location of nucleotide sequences encoding particular antigenic epitopes. Moreover, certain monoclonal antibodies specific for the P1 protein have been shown to inhibit cytadherence of *M. pneumoniae* and, therefore, are specific for the functional domain of P1 that mediates cytadherence. When these monoclonal antibodies are used for screening, the epitopes involved in mediating cytadherence can be mapped as well.

The recombinant DNA clones encoding all or part of the functional domain responsible for cytadherence are particularly valuable. First, the peptides expressed by such clones may be used as immunodiagnostic reagents to detect *M. pneumoniae* infection. More importantly, the peptides may be incorporated into an antimycoplasmal vaccine. In addition, antigenic peptides comprising the cytadhesin specific epitopes can be synthesized, on the basis of the amino acid sequences deduced from the mapped nucleotide sequence and used as vaccines or antigens for immunodiagnostic tests.

Finally, it should be pointed out that, for practical reasons, it may often be easier to demonstrate the P1 cytadhesin epitopes using a monoclonal antibody since polyclonal antiserum will usually contain antibody molecules specific for regions of the P1 protein not associated with the cytadhesin domain as well as antibody molecules specific for cytadhesin epitopes. However, polyclonal antiserum capable of inhibiting P1 mediated cytadherence may also be used to demonstrate presence of the cytadhesin epitopes by a number of techniques generally known to those of skill in the art. For example, selected P1 polypeptides may be used to extensively adsorb the polyclonal antiserum and adsorbed and nonadsorbed antiserum compared for the ability to inhibit cytadherence. By this procedure, specific polypeptides capable of significantly reducing the antibody mediated inhibition of P1 mediated cytadherence may be considered to express cytadhesin epitopes. In addition, cytadhesin epitopes may be demonstrated directly by their ability to competitively inhibit P1 mediated cytadherence in any of a number of experimental systems commonly used to measure cytadherence, described by Morrison-Plummer, et al., *Infect. Immun.*, 53:398 (1986), or Krause and Baseman, *Infect. Immun.*, 39:1180–1186 (1983).

Although the methodology described herein contains sufficient detail to enable one skilled in the art to practice the present invention, a commercially available technical manual entitled *MOLECULAR CLONING* (Maniatis, et al., Cold Spring Harbor Laboratory, Cold Spring Harbor, N.Y.) may provide additional details useful to assist practice of some aspects of the invention. Accordingly, this manual is incorporated herein by reference.

The following examples are designed to illustrate certain aspects of the present invention. However, they should not be construed as limiting the claims thereof.

EXAMPLE I

ISOLATION OF A RECOMBINANT CLONE THAT CONTAINS A DNA SEQUENCE ENCODING M. PNEUMONIAE P1

This example is designed to illustrate the actual steps followed by the inventors in obtaining a specific recombinant clone that contained a DNA sequence encoding the mycoplasma P1 protein. However, tis example is not meant to represent the only procedure for cloning the P1 gene.

A. Culture Of Mycoplasma And *E. Coli*

Virulent hemadsorbing *Mycoplasma pneumoniae* strain M129 in the sixteenth broth passage was grown at 37° C. in 32 ounce glass prescription bottles containing 70 ml of Edward medium (Edward, *J. Gen. Microbiol.*, 1:238–243 (1947)). Glass adherent mycoplasmas were washed four times with phosphate buffered saline (PBS; pH 7.2) and collected by centrifugation (9,500×g 20 min.). Cells were harvested 72 hours after inoculation and stored at −70° C.

*Escherichia coli* strain HB101, DH5 alpha, and JM 107 were purchased from commercial sources and grown in LB broth (10 g/l Bacto-tryptone, 5 g/l Bacto-yeast extract, 10 g/l NaCl, pH 7.5).

B. Purification Of P1 Protein By Affinity Chromatography

The P1 protein was purified by antibody affinity chromatography according to the method described by Leith and Baseman, *J. Bacteriol.*, 157:678–680 (1984). Briefly, this method was as follows.

Four anti-P1 monoclonal antibodies secreted by hybridomas (Morrison-Plummer, et al., *Infect. Immun.*, 55:49–56 (1987); Morrison-Plummer, et al., *Infect. Immun.*, 53:398–403 (1986)) were combined and purified by protein A-Sephadex column chromatography. Anti-P1 affinity columns were prepared by coupling 50 mg of purified anti-P1 antibody to 15 ml of cyanogen bromide activated Sephadex gel (Pharmacia, Piscataway, N.J.).

Pellets from 100 bottles of *M. pneumoniae* were suspended in 50 ml of 20 mM Tris-HCl (pH 8.0), 0.2% sodium deoxycholate (Fisher Scientific), 0.1% sodium dodecyl sulfate (BDH Chemicals, Poole, England), 10 mM EDTA, and 0.2% Triton-X-100 containing 1 mM phenylmethylsulfonyl fluoride. Solubilization of proteins was assisted by passing the cell suspension through successively smaller gauge needles (22 to 27 gauge). Insoluble material was removed by centrifugation at 100,000×g for 30 minutes.

Solubilized proteins were applied to the affinity column at 4° C. and washed with 5 column volumes of the same buffer minus sodium deoxycholate. Bound protein was eluted with 0.1M acetic acid (pH 3) containing 0.15M NaCl and 0.1% SDS. The eluted protein was immediately neutralized with 1.0M Tris and concentrated in a pressure ultrafiltration concentrator (Amicon, Danvers, Mass.).

Figure 1:
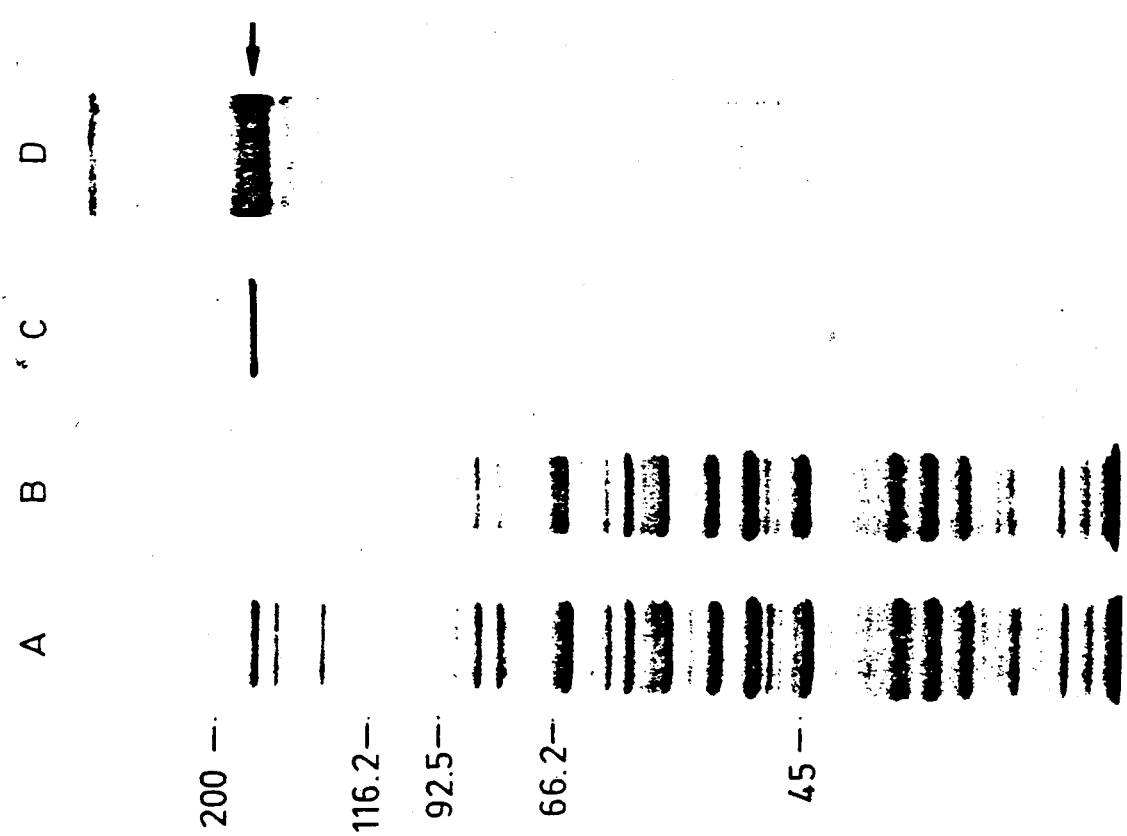

As shown in FIG. 1 (panels A-C), this procedure selectively enriched for the *Mycoplasma pneumoniae* cytadhesin protein P1 (165 kilodaltons). Approximately 400 ug of P1 protein was recovered after the immunoaffinity step from an initial *M. pneumoniae* extract containing 300 mg total protein.

As an additional purification step, the affinity column-purified P1 was further processed by preparative gel electrophoresis through a 5% polyacrylamide-SDS gel. The gel was stained with Coomassie blue and the P1 protein band was cut out of the gel and electroeluted according to the procedure of Hunkapiller, et al. (In Methods in Enzymology, C. H. W. Hirs and S. N. Timasheff (eds.) pp. 227–236 (1983)). About 60% recovery was achieved after 24 hours of elution at room temperature in 50 mM ammonium carbonate containing 0.1% SDS. The eluted protein was then precipitated in 80% methanol to remove SDS. SDS-PAGE analysis of the recovered P1 revealed that the sample contained intact P1 protein (FIG. 1D), and the gel was deliberately overloaded to show the purity of the sample. Finally, the purified protein was shown to be P1 since it reacted with anti-P1 monoclonal antibodies in Western blot analyses (data not shown).

C. Determination Of The N-Terminal Amino Acid Sequence Of P1 Protein And Preparation Of Specific Oligonucleotide Probes The purified P1 protein was sequenced from the amino terminus with a gas phase protein sequencer. Approximately 50 ug of purified P1 was used (300 pmole) for each sequence analysis. Three separate determinations yielded the sequence shown in FIG. 2.

The N-terminal amino sequence was used to deduce sequences for oligonucleotide probes. Two oligonucleotide probes complementary to all the possible mRNA combinations encoding different portions of the protein were synthesized, a 14-mer corresponding to amino acids 1–5 and a 18-mer corresponding to amino acids 7–12 (FIG. 2). The present inventors used both C and T in the third position of the trypotophan codon of the 18 bp oligonucleotide in order to ensure hybridization with the probe in the event that *M. pneumoniae* uses TGA (a stop codon in bacterial and eukaryotic systems) rather than TGG to encode tryptophan. The oligonucleotides were synthesized in the Department of Biochemistry, Baylor College of Medicine according to a procedure similar to that described by Alvarado-Urbina, et al., *Science*, 214:270–274 (1981), incorporated herein by reference, and purified by electrophoresis in 20% polyacrylamide gel containing 8M urea (Berent, et al., *Biotech.*, 3:208–220 (1985)). For use as hybridization probes, the oligonucleotides were labeled at the 5' end with Y-P$^{32}$ATP by the T4-polynucleotide kinase reaction (Maniatis, et al., MOLECULAR CLONING, Cold Spring Harbor Laboratory, Cold Spring Harbor, N.Y. (1982), pp. 122–127).

D. Southern Blot Analysis Of *M. pneumoniae* DNA

*M. pneumoniae* DNA was prepared from exponentially growing cells according to the following procedure. Pellets of *M. pneumoniae* were suspended in 2.7 ml of PBS, lysed by the addition of 0.3 ml of 10% sodium dodecyl sulfate (SDS) and incubated with 10 ug of RNase for 30 minutes at 37° C. Preparations were extracted three times with an equal volume of redistilled phenol (equilibrated with 100 mM Tris [pH 8.0] −10 mM EOTA [TE]) followed by dialysis overnight at 4° C. against a total of 6 liters of sterile TE. Twelve ug of DNA was digested to completion with EcoRI, Hae III, Pst I, Hind III, BamHI, Kpn I or Sal I prior to electrophoretic separation on 0.7% agarose gels. Gels were stained with ethidium bromide and photographed under UV illumination (FIG. 3).

The gels were then analyzed according to the procedure of Southern, *J. Mol. Biol.*, 98:503–519 (1975), incorporated herein by reference. Briefly, DNA was transferred to nitrocellulose filter paper with 20×SSC (0.3M sodium citrate, pH 7.0, 3M NaCl), rinsed once with 6×SSC, then baked at 80° C. for 2 hours under vacuum. Filters were prehybridized overnight at 37° C. in 20 ml of prehybridization solution containing 6×SSC, 60 mM sodium phosphate (pH 7.0), 5×Denhardt's solution (bovine serum albumin, polyvinylpyrolidone, Ficoll at 1 mg/ml) and 0.1 mg/ml of denatured herring sperm DNA.

Hybridizations with the 14 base pair [bp] and 18 base pair [bp] oligonucleotide probes were carried out for 12 hours in 10 ml of prehybridization solution plus 10% dextran sulfate and $^{32}P$ labeled oligonucleotide probes ($3 \times 10^8$ cpm) at 25° C. (14 bp, 14-mer) or 37° C. (18 bp, 18-mer). After incubation, filters were rinsed twice with 6×SSC at 4° C. (30 min. each), then washed twice in wash solution (3M tetramethylammonium chloride, 50 mM Tris-HCl, pH 8.0, 2 mM EDTA, 0.1% SDS) at the appropriate temperature (14-mer at 37° C. and 18-mer at 45° C.) for 20 min. according to the procedure of Wood, et al., *Proc. Nat. Acad. Sci., U.S.A.*, 82:1585–1588 (1985). After washing, filters were rinsed in 6×SSC at 4° C., dried and exposed to X-ray film using an intensifying screen.

Figure 4:
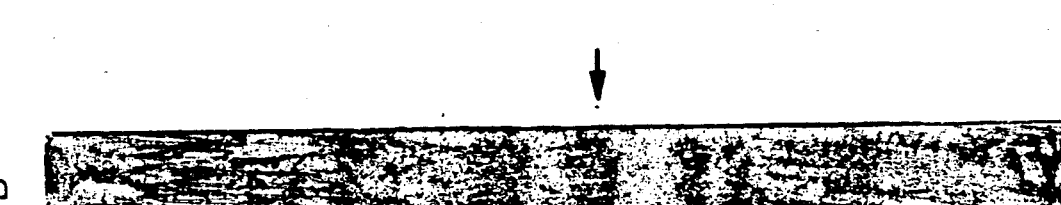

Both probes hybridized to several DNA bands in each digestion, possibly because the probes were comprised of a mixture of oligonucleotides formulated to react with all possible nucleotide sequences that could encode the 12 N-terminal amino acids. A 4.3 kb Hind III fragment hybridized most intensely to both the 14-mer and 18-mer (FIG. 4) strongly implicating this DNA fragment as containing the N-terminal sequence of P1.

E. Cloning DNA Fragments Encoding *M. pneumoniae* P1 Protein

To clone the DNA fragment described above, *M. pneumoniae* DNA was digested with Hind III, separated by agarose gel electrophoresis, and stained briefly with ethidium bromide. DNA in the 4.3 kb size range was eluted from the gel by electrophoresis onto DE-81 paper, eluted from the paper with 20 mM Tris-HCl, pH 8.0, and 1.5M NaCl, then precipitated with ethanol and redissolved in TE buffer.

The DNA was then ligated into the Hind III site of pUC 9. For this procedure, the plasmid was digested with an appropriate restriction enzyme (Hind III) and the 5' end phosphate removed by calf intestinal alkaline phosphatase according to the procedure described on page 133 of Maniatis, et al., *MOLECULAR CLONING*, Cold Spring Harbor Laboratory, Cold Spring Harbor, N.Y. (1982). Mycoplasma DNA and vector were mixed at 1:1 molar ratio ad ligated at room temperature for 4 hours with T4 DNA ligase. After incubation, the reaction was stopped by adding EDTA to 10 mM, diluted 5-fold with distilled H2O.

The ligated plasmid DNA was then used to transform competent HB101 or DH5 alpha *E. coli* cells according to the manufacturer's instructions (BRL, Bethesda, Md.). Transformants were selected on LB agar plates containing 50 ug/ml of ampicillin. About 5,000 transformants were obtained, of which 200 individual colonies were picked and grown overnight in 5 ml of LB broth containing 50 ug/ml of ampicillin. Plasmid DNA was isolated from overnight cultures by the alkaline lysis method (Ish-Horowicz and Burke, *Nucleic Acid Res.*, 9:2989–2998 (1981)) and analyzed on agarose gels.

Figure 5:
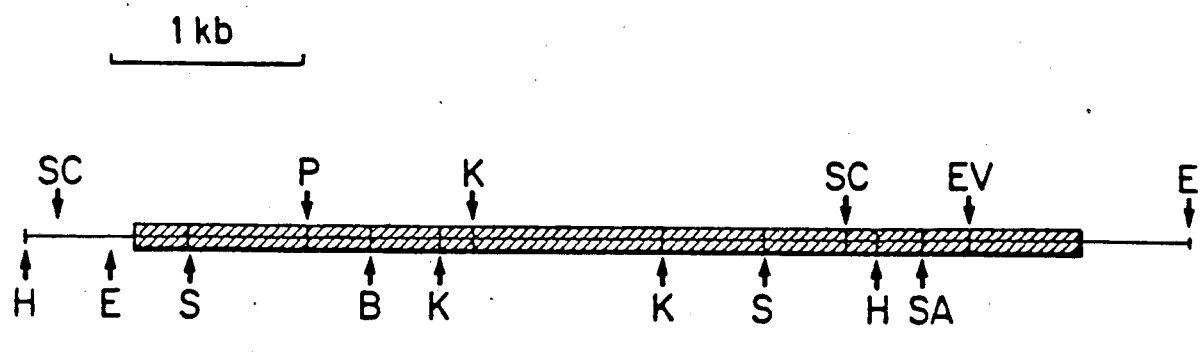
Figure 7:
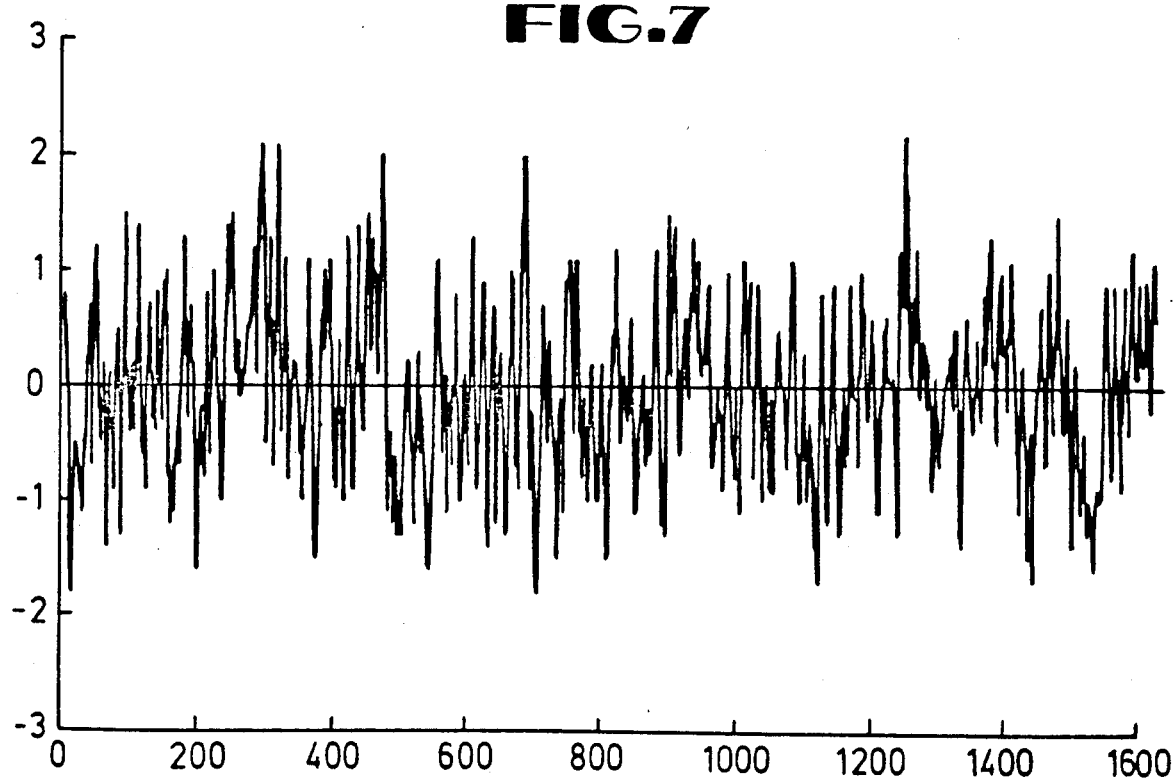

To determine which insert-containing plasmids carried the P1 gene, DNAs from about 40 plasmids with inserts in the 4–5 kb range were blotted onto nitrocellulose filters. The filters were then hybridized to the $^{32}P$ labeled 14-mer and 18-mer oligonucleotide probes, washed and exposed to film as described above. Three clones hybridized strongly to both probes. By restriction endonuclease analysis the three clones contained the same insert designated 62A (FIG. 5).

Figure 6N:
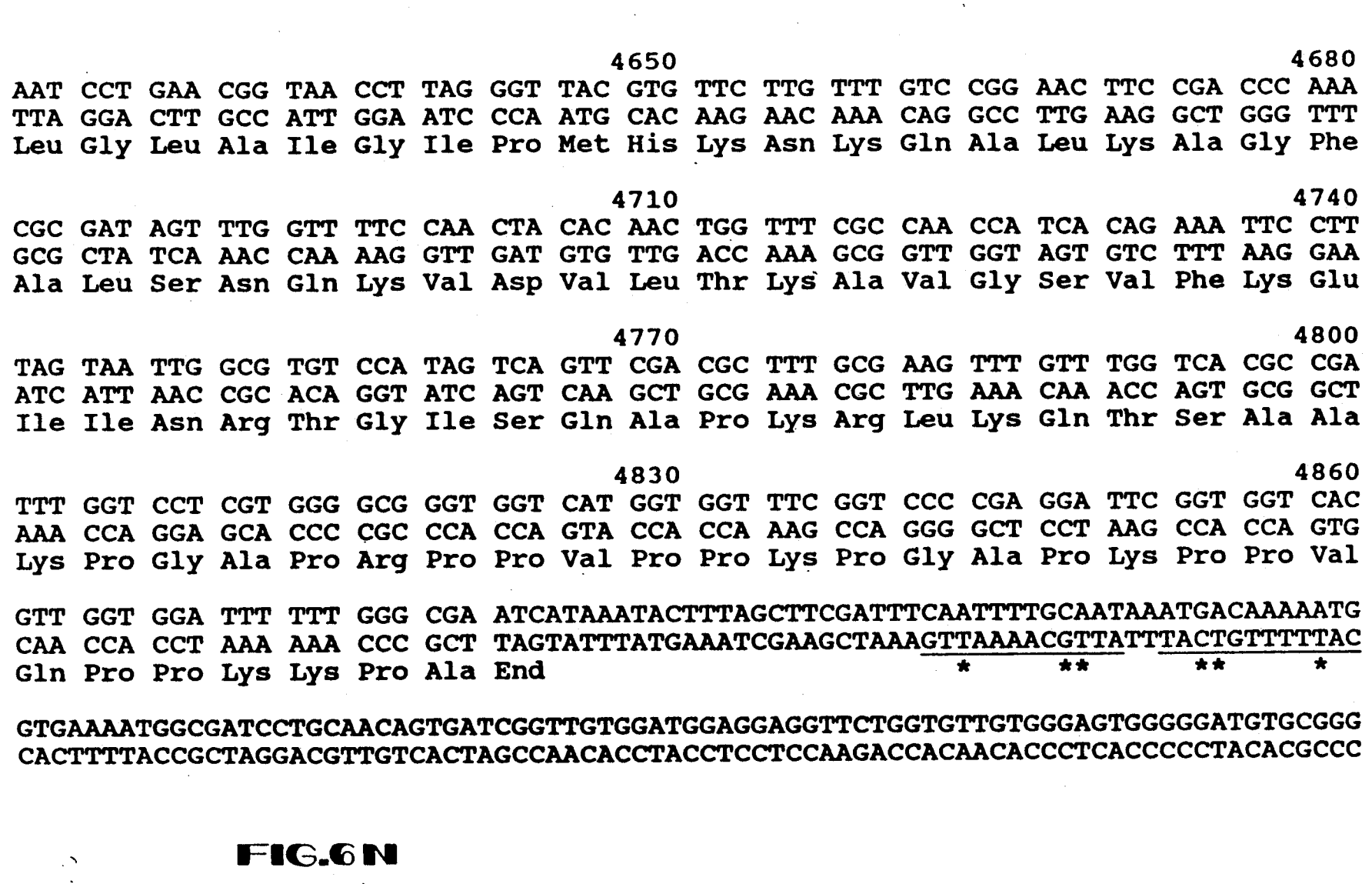

The DNA sequence which hybridized to both probes was narrowed to a 350 bp Hae III restriction fragment by digesting the 62A plasmid with the Hae III, separating the DNA on a 5% polyacrylamide gel, and transferring the DNA from the gel onto nitrocellulose paper for hybridization with each individual probe (data not shown). The 350 bp Hae III piece was subcloned into M13mp18 and its sequence determined. It contains both the 14-mer and 18-mer sequences, and most importantly the DNA has an open reading frame which codes for the 18 amino acids found by sequencing the amino terminus of the P1 protein (FIG. 6). Thus, clone 62A was shown to contain at least a part of the structural gene encoding P1.

However, based upon the location of the sequenced Hae III fragment in the 62A clone, the 4.3 kb Hind III DNA fragment was not large enough to encode the entire 165 kDa P1 protein. Therefore, an EcoRI/Pst I restriction fragment from 62A was used to clone a larger DNA fragment. This procedure was performed as follows:

Plasmid 62A was isolated from overnight cultures by the alkaline lysis method (Ish-Horowicz and Burke, *Nucleic Acids Res.*, 9:2989–2998 (1981)) and digested to completion with a mixture containing 500 units EcoRI and 500 units Pst I. The resulting restriction fragment was purified by agarose gel electrophoresis, labeled by nick translation (Maniatis, et al., *MOLECULAR CLONING*, Cold Spring Harbor Laboratory, Cold Spring Harbor, N.Y. (1982), pp. 109–112) and used to probe Southern blots of *M. pneumoniae* DNA digested to completion with EcoRI. This procedure was performed essentially as described above, except that the hybridization conditions were more stringent including a higher temperature of hybridization and wash (65° C.).

By this procedure, an *M. pneumoniae* DNA fragment approximately 6 kbp was detected. Accordingly, DNA in this size range was eluted from an agarose gel of the EcoRI-digested DNA by electrophoresis onto DE-81 paper, eluted from the paper with 20 mM Tris-HCl, pH 8.0, and 1.5M NaCl, then precipitated with ethanol and redissolved in TE buffer.

The DNA was then ligated into the EcoRI site of pUC 19, essentially as described above and used to transform *E. coli*, as described above. Restriction enzyme analysis of the cloned insert indicated that the 6 kbp insert overlapped clone 62A and was sufficiently large to encode the entire P1 protein. The restriction enzyme map depicting both the 4.3 kbp Hind III fragment and the 6 kbp EcoRI fragment is shown in FIG. 5.

EXAMPLE II

DETERMINATION OF THE COMPLETE DNA SEQUENCE OF THE GENE ENCODING MYCOPLASMA PNEUMONIAE P1 AND DEDUCTION OF THE COMPLETE AMINO ACID SEQUENCE OF THE P1 PROTEIN

A. Sequencing Of The P1 Gene

DNA sequences were determined by the dideoxy-chain-termination method of Sanger, et al., *Proc. Natl. Acad. Sci., U.S.A.*, 74:5463-5467 (1977). M13 sequencing kits were purchased from BRL and the reactions were performed according to the manufacturer's instructions except deoxy-7-deaza GTP (Boehringer Mannheim, Indianapolis, Ind.) was used in sequencing reactions in place of dGTP (Messing, et al., *Nuc. Acid Res.*, 9:309-321 (1981)). Some DNA fragments were sequenced by subcloning appropriate restriction enzyme fragments into an M13 phage vector (Messing, et al., *Nuc. Acids Res.*, 9:309-321 (1981)) and the single strand DNA purified for use as a sequencing template. To sequence the rest of the P1 gene, a large piece of DNA from the Pst I to the Sal I (see FIG. 5) was subcloned into an M13 vector and a series of deletions from the 3' end were generated by treating the double strand DNA with exonuclease III according to the method of Heinkoff, *Gene*, 28:351-359 (1981). Subclones with progressive deletions were selected for use as sequencing templates. Both strands of the entire P1 gene were sequenced. Nucleic acid and protein computer analyses were performed using the Microgenie program (Beckman, Palo Alto, Calif.). Comparisons of the P1 DNA and deduced protein sequences were to the most recent releases of the NIH Genbank DNA sequence database and the National Biomedical Research Foundation protein sequence database, respectively.

B. Analysis Of The P1 Nucleotide Sequence

The nucleotide sequence of the P1 gene is shown in FIG. 6. There is an open reading frame of 4881 nucleotides and at the end of the gene is a TAG stop codon followed by 2 in-frame TAA stop codons 21 and 27 bp downstream. This sequence could encode a protein of 1627 amino acids with a calculated molecular weight of 176,288.

The nucleotide sequence includes a possible in frame translation initiation site, ATG, 177 nucleotides from the P1 N-terminal sequence. There are conventional transcription initiation sites at −35 and −10 upstream with a distance of 14 nucleotides between these two consensus sequences (Reznikoff, et al., *Ann. Rev. Genet.*, 19:355-387 (1985)), but no ribosomal binding site is observed between −10 and the initiation codon. This predicts a protein with an extension of 59 amino acids from the N-terminus. Another possible translation initiation codon is the GTG (Gold, et al., *Ann. Rev. Microbiol.*, 35:365-403 (1981)) at position 91. Use of this initiation site would predict a 28 amino acid precursor.

The open reading frame contains the 18 amino acids identified by gas phase sequencing (FIG. 6, Box). Comparison of the gas phase sequence with the nucleotide sequence demonstrates that the inventors' hunch that *M. pneumoniae* might use this codon to encode tryptophan was correct.

Moreover, it was observed that the 18 amino acids are found at position 60-77 of the deduced protein instead of at the amino terminus of the open reading frame. The reason for this apparent discrepancy could well be that P1, like many outer membrane proteins, is initially synthesized as a precursor (Oliver, *Ann. Rev. Microbial.*, 39:615-648 (1985)). Consistent with this hypothesis is the observation that the extra 59 amino acids found at the amino terminus of the deduced protein appear like a signal peptide; they include positively charged amino acids followed by a stretch of hydrophobic amino acids (Oliver, *Ann. Rev. Microbial.*, 39:615-648 (1985)). If protein p1 is indeed synthesized as a precursor and processed into a mature protein, then the molecular weight of the mature protein would be 169,758 which is very close to the 165 kDa reported earlier [Baseman, et al., *J. Bacteriol.*, 151:1514-1522 (1982); Krause, et al., *Infect. Immun.*, 35:809-817 (1982); Leith and Baseman, *J. Bacteriol.*, 157:678-680 (1984); and Morrison-Plummer, et al., *Infect. Immun.*, 55:49-56 (1987)] and almost identical to the value (168 kDa) determined by Jacobs, et al., *J. Clin. Microbiol.*, 23:517-522 (1986) on SDS-PAGE.

Other relevant features of the sequence include a typical eubacterial promoter (Reznikoff, et al., *Ann. Rev. Genet.*, 19:355-387 (1985)) for RNA polymerase which is upstream of the first ATG codon, at approximately −35 and −10. Also, a not-so-perfect invert repeat sequence is detected 19 base pairs downstream from the TAG stop codon. The inverted repeat sequence is a common feature of an RNA terminator (Rosenberg and Court, *Ann. Rev. Genet.*, 13:319-353 (1979)). However, no typical ribosomal binding site is observed between −10 and the initiation codon.

C. Determination Of The Amino Acid Sequence Of The P1 Protein

The complete amino acid sequence of the *M. pneumoniae* (FIG. 6) P1 protein was predicted from the DNA sequence, also shown in FIG. 6. The predicted amino acid sequence is consistent with available information about protein P1: the predicted molecular weight of P1 approximates the reported values; and the predicted N-terminal amino acid sequence fits exactly with the gas phase sequence analysis of purified P1 protein. The predicted P1 sequence contains more basic amino acids (Arg+Lys+His=169) than acidic (Asp=Glu=143) (isoelectric focusing data shows that P1 has an isoelectric point at a basic pH). The predicted P1 contains no cysteine and thus has no intramolecular disulfide bonding, a finding which correlates with the previous observation that the P1 position in polyacrylamide gels is not changed after exposure to sample buffer containing reducing agents.

By referring again to FIG. 6, it can be seen that the predicted P1 protein has several other interesting features: a) it contains high percentages of hydroxy amino acids (17.7% are serine and threonine); and the high proline content (13 of 26 amino acids) at the carboxy terminus is unusual and may place structural restraints on the protein and assist in regulating the topological organization of the cytadhesin in the membrane [Baseman, et al., *J. Bacteriol.*, 151:1514-1522 (1982); Baseman, et al., In Molecular Basis of Oral Microbial Adhesion, S. E. Mergenhagen and B. Rosan (eds.), (1985); Kahane, et al., *Infect. Immun.*, 49:457-458 (1985); and Krause, et al., *Infect. Immun.*, 35:809-817 (1982)].

It should be noted that FIG. 6 displays the actual nucleotide sequence determined by sequence analysis of the 6 kbp EcoRI fragment (plasmid pMPN P1) insert obtainable from ATCC #67560. As those of skill in the art will appreciate, due to the redundancy of the genetic code, numerous other nucleotide sequences may be constructed which code for the same amino acid sequence. Therefore, any nucleic acid sequence encoding for the *M. pneumoniae* P1 protein as depicted in FIG. 6 is meant to be included within the scope of the present invention. This includes nucleotide sequences containing either the mycoplasmal (TGA) or traditional (TGG) tryptophan codons.

D. Homology Between *M. pneumoniae* And Other Proteins Having Known Amino Acid Sequences The deduced amino acid sequence for the P1 protein was compared to known amino acid sequences listed in the National Biomedical Research Foundation protein sequence database. This analysis revealed that the predicted P1sequence is homologous to coat protein A of bacteriophage Ike (protein P1 amino acid numbers 1308 through 1322 compared to bacteriophage amino acid numbers 240 through 254, 73.3% homology; 257-290 vs. 231-264, 41.2% homology), protein 3A of Brome Mosaic virus (956-979 vs. 133-159, 52% homology), coat protein vp2 and vp3 of mouse polyomavirus (733-746 vs. 24-38, 66.7% homology), and coat protein A precursor of bacteriophage fd, M-13 and Fl (1296-1330 vs. 245-280, 51.3% homology). The 1290-1350 region of P1 also shares extensive homology With cytoskeletal keratin of mammalian species. In addition, two regions of P1 share extensive homology with human fibrinogen alpha chain precursor (337-352 vs. 338-354, 70.6% homology; 822-852 vs. 544-565, 59.1% homology). It is fascinating that parts of the P1 sequence are homologous to specific viral coat proteins, mammalian cytoskeletal keratin and to human fibrinogen alpha chain precursor. These findings may help explain observations of autoimmune-like mechanisms of physiopathology associated with mycoplasma disease (Biberfeld, S., *Clin. Exp. Immunol.*, 8:319-333 (1971); Wise and Watson, *Infect. Immun.*, 48:587-591 (1985)).

E. Analysis Of Individual Antigenic Determinants Within The P1 Molecule By Hydrophillicity Plotting Cytadhesin P1 is strongly immunogenic and the appearance of anti-P1 antibodies correlates with resolution of the atypical pneumoniae induced by *M. pneumoniae*. Therefore, the recombinant P1 protein or selected peptides derived from the P1 protein provide attractive vaccine candidates. The present inventors have performed experiments directed towards mapping individual antigenic sites within the protein. One approach is used to map the antigenic sites and is described below.

In general, antigenic sites are usually hydrophilic. Therefore, where the amino acid sequence of a protein is known, hydrophilicity plots may be constructed which allow one to predict the location of antigenic determinants (Hopp and Woods, *Proc. Natl. Acad. Sci., U.S.A.*, 78:3824-3828 (1981)). Hydrophilicity plotting of the predicted *M. pneumoniae* P1 sequence was performed using the Microgenie program obtained from Beckman (Palo Alto, Calif.). This analysis revealed potential antigenic sites (FIG. 7) at positions 240-260, 280-304, 314-333, 450-479, 680-690, 746-767, 898-913, 1244-1260, and 1476-1485.

EXAMPLE III

EXPRESSION OF THE COMPLETE RECOMBINANT P1 PROTEIN

The following prophetic example is intended to describe methods by which the P1 gene could be expressed to provide a complete P1 protein.

The P1 protein could be expressed by ligating the piece of DNA that includes the first Hind III site through the second EcoRI site (see FIG. 5) to a mycoplasma compatible vector, such as *E. coli* plasmid pAM120, then transforming fast growing mycoplasma species (such as Acholeplasma) for production of large quantities of P1. (See Dybvig, K., et al., *Science*, 235:1392 (1987), which is incorporated herein by reference.)

The P1 gene could also be modified to express whole P1 in *E. coli.* All the UGA codons in the structural gene of P2 could be changed into UGG by site specific mutagenesis. See Shortle, D., et al., *Meth. in Enzymol.*, 100:457 (1983), which is incorporated herein by reference. Then a powerful *E. coli* promoter such as the lac promoter could be ligated to the P1 gene to overproduce P1. Alternatively, an *E. coli* strain with UGA suppressor phenotype (Raftery, L., et al., *J. Bacteriol.*, 158:849 (1984), which is incorporated herein by reference) could be used as host to express the unmodified P1 gene.

Also, the P1 gene promoter is a unique mycoplasma promoter which can be used for the expression of other proteins in mycoplasma species.

EXAMPLE IV

CLONING, SEQUENCING, AND EXPRESSION OF NUCLEOTIDE SEQUENCES ENCODING THE FUNCTIONAL CYTADHESIN BINDING DOMAIN OF *M. PNEUMONIAE*

This example describes the construction of the lambda gt11 recombinant DNA expression library of *M. pneumoniae* used to characterize the P1 domain involved in cytadherence. In general, clones expressing P1 epitopes were identified by screening the library with two anti-P1 monoclonal antibodies known to block *M. pneumoniae* attachment to erythrocytes (RBCs) and respiratory epithelium.

A. Construction Of The Lambda gt11 Library

1. Bacteria, Vector, and Restriction Enzymes

*M. pneumoniae* strain M129-B16 was cultured as described in Example I. *E. coli* Y1088 (American Type Culture Collection (ATCC #37195), Y1089 (ATCC #37196), and Y1090 (ATCC #37197) were cultured in LB medium. These cell lines are available through the American Type Culture Collection or from Clontech Laboratories (Palo Alto, Calif.).

Lambda gt11 DNA arms and phage extracts were purchased from Promega Biotech (Madison, WI). Enzymes used for constructing the genomic library were from New England Biolabs (Beverly, MS); restriction enzymes were from BRL (Gaitherburg, Md.).

2. Construction Of The *M. pneumoniae* Genomic Library In Lambda gt11

*M. pneumoniae* strain M129-B16 genomic DNA library was constructed in the expression vector lambda gt11 according to general procedures described by Young and Davis, *Proc. Natl. Acad. Sci.*, 80:1194-1198 (1983) and *Science*, 222:778-782 (1983) incorporated herein by reference.

More specifically, mycoplasmal DNA was extracted and fragmented as described in Example I, but using mechanical shearing in place of restriction endonucleases.

The sheared DNA was then ligated to EcoRI linkers, and these DNA fragments were ligated into the EcoRI site in lambda gt11 arms essentially as described by Young and Davis, *Proc. Natl. Acad. Sci.*, 80:1194 (1983) and *Science*, 222:778 (1983). Briefly, this procedure comprises incubating the vector DNA and the *M. pneumoniae* DNA fragments at high vector/insert ratio of 2:1 in ligation buffer (0.066M Tris-HCl, pH 7.5; 5 mM $MgCl_2$; 5 mM DTT; 1 mM ATP) with 1U T4 DNA ligase at 12° C. for 2-16 hours.

Recombinant DNA was packaged to provide viable phage according to instructions provided by the commercial supplier of the phage arms and phage extracts (Promega Biotech, Madison, Wis.). Alternatively, packaging extracts may be prepared and packaging reactions carried out according to protocols described on pages 256-268 of *MOLECULAR CLONING*.

The phage may then be tittered by plating a small number of phage from the packaging mix (about 100) on *E. coli* Y1088 at 42° C., using 2.5 ml LB soft agar (pH 7.5) containing 40 ul of 40 mg/ml × gal and 40 ul of 1MPTG for a 90 mm Petri dish. Plaques produced by the parental lambda gt11 phage are blue, while plaques produced by the recombinant phage are colorless. (In a few cases, particular recombinant phage plaques will produce a slight amount of blue color.)

The library may then be amplified by plating out the library at a density of $10^6$ p.f.u. per 150 mm Petri dish, using 600 ul of Y1088 plating cells per dish and fresh LB plates and incubating at 42° C. Plate stocks may be prepared as described by Davis, et al., *Bacterial Genetics*, Cold Spring Harbor Laboratory, Cold Spring Harbor, N.Y. (1980).

Alternatively, it is possible to screen the lambda gt11 library without amplification. For this procedure, 0.1 ml Y1088 plating cells are infected with $\leq 10^5$ plaque forming units at 37° C. for 15 minutes. Then 0.5 ml of Y1090 plating cells and 7.5 ml LB soft agar are added. The mixture is poured into a two-day old 150 mm LB plate (pH 7.5).

B. Screening Lambda gt11 *M. pneumoniae* DNA Libraries With Monoclonal Antibody Probes The *M. pneumoniae* DNA phage library was screened with a pool of two anti-P1 monoclonal antibodies directed against unique *M. pneumoniae* epitopes involved in cytadherence. The screening procedure was generally performed as follows.

*E. coli* Y1090 was grown to saturation in LB (pH 7.5) at 37° C. and 0.6 ml of the Y1090 culture was mixed with up to $10^5$ p.f.u. in lambda diluent for each plate. The phage were absorbed to the cells at 37° C. for 15 minutes. Then 7.5 ml of LB soft agar (pH 7.5) was added to the culture and the mixture was poured onto an LB plate (pH 7.5). The plates were incubated at 42° C. for 3-4 hours and then placed at 37° C. Each plate was then overlayed with a dry nitrocellulose filter disk which had been saturated in 10 mM IPTG in water. The plates were then incubated for an additional 2-3 hours at 37° C. and removed to room temperature. The filters were then removed from the plate and the following steps were performed.

First, the filters were rinsed briefly in TBS (50 mM Tris-HCl, pH 8.0, 150 mM NaCl) and incubated in TBS plus 20% fetal calf serum for 15-30 minutes. The filters were then incubated in TBS plus 20% fetal calf serum plus a mixture containing 1 ug/ml MAb6E7 and 2 ug/ml MAb5B8 for one hour. Preparation of these antibodies is described in Plummer, et al., *Infect. Immun.*, 53:398-403 (1986), incorporated herein by reference.

The filters were then washed in TBS for 5-10 minutes, washed again in TBS plus 0.1% NP-40 for 5-10 minutes, rewashed in TBS alone for 5-10 minutes, rinsed briefly in TBS plus 20% fetal calf serum, and transferred to TBS plus 20% fetal calf serum containing horseradish peroxidase-conjugated to goat anti-mouse immunoglobulin. The filters were then washed again in TBS, TBS plus 0.1% NP-40, and TBS. The filters were dried and 4-chloro-1-naphthol was used as substrate to develop the immunoblots.

When the lambda gt11 *M. pneumoniae* genomic library was screened with the two monoclonal antibodies, ten independent clones that produced strong signals were isolated. Eight of the clones reacted with both monoclonal antibodies, one clone (P1-7) reacted only with MAb6E7 and another clone (P1-10) reacted only with MAb5B8. The nucleotides encompassed by each of these clones is indicated by FIG. 8.

C. Analysis Of The Recombinant Phage Clones

The following experiments were performed in order to further characterize the mycoplasmal proteins produced by the recombinant phage. Positive signal-producing phage were grown in *E. coli* Y1090 as described in *MOLECULAR CLONING*, pp. 64-65. DNA was extracted by a rapid small-scale plate lysate method using 2 units of EcoRI to excise the *M. pneumoniae* DNA inserts essentially as described in *MOLECULAR CLONING*, pp. 371-372.

1. Sequencing Of the *M. pneumoniae* DNA Inserts

DNA sequences of the recombinant phage inserts were determined essentially as described in Example II. The results of this analysis are shown in FIGS. 8 and 9. By comparing the sequences of these clones to the complete P1 gene sequence (FIG. 6), the cytadhesin binding domain of the *M. pneumoniae* P1 protein was mapped to the C-terminal region of the P1 gene. The sequences of three clones were of particular utility in further mapping antigenic epitopes of P1. These clones were P1-7, P1-9, and P1-10. As shown in FIG. 9, clone P1-7 starts at position 4067 and ends at position 4185; clone P1-9 starts at position 4148 and extends beyond the end of the P1 gene. These two clones both contain nucleotides 4148-4185. These nucleotides code for a P1 polypeptide thirteen amino acids in length, the thirteen amino acids that contain the epitope reactive with the cytadherence-blocking MAb6E7. Clone P1-10 starts at position 4202 and extends beyond the P1 gene. This clone is nonreactive with MAb6E7, yet shares a stretch of nucleotides that overlap with clone P1-9; further demarcating the thirteen amino acid cytadherence related epitope.

Therefore, a key domain of adhesion P1 that mediates the cytadherence of virulent *M. pneumoniae* to respiratory epithelium has been mapped to a thirteen amino acid region located in the C-terminal end of the P1 molecule. In addition, the present studies have established that a second cytadhesin epitope, recognized by MAb5B8, is C-terminal to position 4202. Therefore, the C-terminal end of the P1 protein appears to be the primary effector region of the P1 molecule. It is interesting that the carboxy terminus of the P1 protein is proline rich (13 of the last 26 amino acids are proline). This hydrophobic domain may function to anchor the carboxy terminal end of the P1 molecule in the *M. pneumoniae* membrane.

2. The Thirteen Amino Acid Cytadhesin Epitope Is Unique To *M. pneumoniae* P1

By comparing the sequence of the P1-7 probe to the known DNA sequence of the complete P1 gene, it was determined that the P1 molecule contained only one copy of the thirteen amino acid epitope described above. However, it was of interest to determine whether or not this epitope was unique to *M. pneumoniae*. Therefore, the following experiment was performed.

Figure 10:

Mycoplasma DNA was digested with different restriction enzymes (BamHI, EcoRI, Hind III, Pst I, Sac I, Sma I) and fractionated by agarose gel electrophoresis, essentially as described in Example ID above. However, the DNA insert from clone P1-7 was used as a hybridization probe. Hybridization was carried out at 68° C. overnight according to Maniatis, et al., *MOLECULAR CLONING*, Cold Spring Harbor Laboratory, Cold Spring Harbor, N.Y. (1982), pp. 382-289. The results of this procedure, shown in FIG. 10, clearly demonstrate that the cytadherence related epitope of clone P1-7 occurs only once in the *M. pneumoniae* genome.

D. Analysis Of *M. pneumoniae* P1 Cytadhesin Peptides

The following studies were undertaken to further characterize the cytadhesin polypeptides produced by the recombinant lambda gt11 bacteriophage.

It will be appreciated by those familiar with the lambda gt11 fusion system, that the site used for insertion of foreign DNA is a unique EcoRI cleavage site located within the lacZ gene, 53 base pairs upstream from the beta-galactosidase translation termination codon. Because the site of insertion for foreign DNA in lambda gt11 is within the structural gene for beta-galactosidase, foreign DNA sequences in this vector have the potential to be expressed as fusion proteins with beta-galactosidase. The position within the beta-galactosidase gene chosen for fusion with foreign DNA sequences, corresponds to a region near the carboxy terminus of the beta-galactosidase protein.

Fusion proteins expressed by the recombinant clones of the present invention were analyzed by Western blotting. This procedure was performed essentially as follows. *M. pneumoniae* protein (2 mg) was suspended in 0.3 ml of PBS, and an equal volume of 100 mM Tris (pH 6.8) −2% S.D.S. −20% glycerol −2% 2-mercaptoethanol-0.02% bromophenol blue buffer (SP buffer) was added. Samples were boiled for 5 minutes. Recombinant fusion proteins were harvested from plate lysates of individual clones by scraping soft agarose overlays from the plates, passing them through a 22 gauge needle into a Corex tube and eluding with 4 m of SM buffer for two hours at 4° C. The agarose was pelleted by centrifugation at 10,000×g for 15 minutes at 4° C. prior to trichloracetic acid precipitation of the supernatant by the addition of cold trichloracetic acid, for a final concentration of 10%. Samples were incubated at 4° C. overnight prior to centrifugation at 10,000×g for 20 minutes at 4° C. Supernatants were discarded, and pellets were washed twice with 1 ml of PBS, suspended in 200 ul of SP buffer, and neutralized with 1 ul of 5 N NaOH. Samples were boiled for 5 minutes and solubilized proteins were electrophoresed on a 5.0% polyacrylamide gel prior to electrophoretic transfer to nitrocellulose paper (Towbin, et al., *Proc. Natl. Acad. Sci., U.S.A.*, 76:4350-4354 (1979)).

After protein transfer, the nitrocellulose was cut into strips and reacted with a pool of the two MAbs (monoclonal antibodies) designated 5B8 and 6E7. For this procedure, nitrocellulose blots were blocked in 1.5% bovine serum albumin (BSA) −1.5% gelatin in TBS for 3-4 hours prior to incubation with the pooled monoclonal antibodies. The final concentration of the antibodies in the reaction mixture was 2 ug/ml 5B8 and 1 ug/ml 6E7 in a buffer comprising TBS plus 20% FCS. Blots were incubated with the diluted antibody preparation overnight at room temperature with shaking, following by three ten minute washes with TBS. Horseradish peroxidase-conjugated goat anti-mouse IgG diluted 1:2000 in TBS containing 0.75% BSA −0.75% gelatin was added to the blots and incubated with shaking for 3-4 hours at room temperature. Blots were washed three times for ten minute periods with TBS prior to substrate development.

Figure 11:
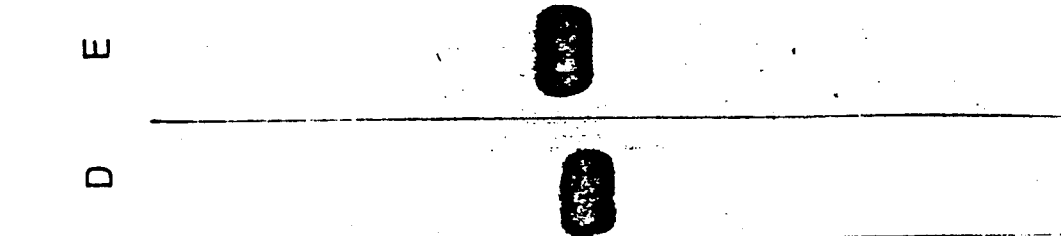

The results of this procedure, shown in FIG. 11, show the representative clones produced fusion proteins larger than the control lambda gt11 beta-galactosidase protein. However, except for clone P1-7, the size of each fusion protein was much smaller than that predicted from the size of the corresponding recombinant DNA insert. This finding may be explained as resulting from early termination of the cytadhesin peptide due to the presence of the TGA codon at position 4556. The present inventors have discovered that *M. pneumoniae* utilizes this codon for tryptophan, while *E. coli* reads UGA as stop signal. Therefore, when *E. coli* is used as a host for a vector containing the recombinant Pneumoniae insert, a prematurely truncated polypeptide may be produced.

E. Cytadhesin Peptides Can Be Used For Serodiagnosis Of *M. pneumoniae* Infection Studies have shown that adhesion P1 is highly immunogenic (Hu, et al., *Science*, 216:313-315 (1982)) and patients infected with *M. pneumoniae* exhibit neutralizing antibodies to the P1 adhesion (Leith, et al., *J. Exp. Med.*, 157:502-516 (1983)). Since the isolated clones express P1 cytadhesin peptides, these clones were analyzed for reactivity with sera of patients with early and late stages of *M. pneumoniae* infection. Normal human sera was used as a control. These experiments were performed by the immunophage blot method. Briefly, this procedure was performed as follows. Individual recombinant phages were dotted on a lawn of *E. coli* Y1090. The plates were incubated at 42° C. for 3-5 hours. Then a nitrocellulose filter (HAHY, M) previously saturated with 10 mM IPTG was overlayed on individual plates and incubation continued at 37° C. overnight. Filters were removed and reacted with sera from *M. pneumoniae* infected patients or normal human controls essentially as described in FIG. 12 using horseradish peroxidase-conjugated goat anti-human immunoglobulin, and 4-chloro-1-naphthol to develop the immunoblots.

The results of this procedure, shown in FIG. 12, indicated that fusion proteins produced by all ten anti-P1 MAb reactive clones also reacted with acute and convalescent sera of *M. pneumoniae* infected patients but did not react with normal human serum. Therefore, the cytadherence related P1 peptides or fusion proteins described herein may be used for serodiagnosis of patients infected with *M. pneumoniae*.

F. Preparation Of Recombinant Antigens From The Lambda gt11 Recombinant Clones It is often useful to have preparative amounts of polypeptides specified by a cloned piece of DNA. For some purposes, for instance, radioimmunoassays, it is sufficient to have a crude *E. coli* lysate containing an antigen specified by the cloned DNA of interest. This prophetic example illustrates how a crude lysate containing a cytadhesin peptide fusion protein can be prepared by expressing a lambda gt11 recombinant as a lysogen in *E. coli* 1089 (*E. coli* Delta lac U169 proA+Delta lon ara D139 strA hsl A150 [chr::Tn10] (p MC9)). The recombinant fusion protein would be produced by lysogenizing Y1089 with the lambda gt11 clone of interest. The lysogen would be grown to high cell density, lacZ-directed fusion protein production induced by the addition of IPTG to the medium, and the cells harvested and lysed.

More specifically, the Y1089 cells would be grown to saturation in LB medium (pH 7.5/0.2% maltose) at 37° C. and then infected with the selected lambda gt11 recombinant phage (preferably P1-7) at a multiplicity of approximately 5 for 20 minutes at 32° C. in LB medium (pH 7.5) supplemented with 10 mM $MgCl_2$ The cells would then be plated on LB plate at a density of approximately 200/plate and incubated at 32° C. At this temperature, the temperature sensitive phage repressor is functional. Single colonies would be tested for temperature sensitivity at 42° C. by spotting cells from single colonies using sterile toothpicks onto two LB plates. The first plate would be incubated at 42° C. and the second at 32° C. Clones growing at 32° C. but not at 42° C. are assumed to be lysogens. Lysogens should arise at a frequency between 10% and 70%.

The crude lysate would then be prepared from the lambda gt11 recombinant lysogen by incubating 100 ml of LB medium with a single colony of the Y1089 recombinant lysogen at 32° C. with aeration. When the culture has grown to an optical density of 0.5 measured at 600 mm, the temperature of the culture would be increased to 42°-54° C. as rapidly as possible and the culture incubated at the elevated temperature for 20 minutes with good aeration. IPTG would be added to 10 mM and the culture is incubated at 37°-38° C. for approximately one hour. At this stage, the Y1089 lysogen will sometimes lyse, even though the Y1089 does not suppress the mutation, causing defective lyses (S100) in lambda gt11. The reason for this is that the S100 amber mutation is leaky and foreign proteins accumulating in *E. coli* often render it susceptible to lysis. Therefore, the longest incubation time achievable at 37°-38° C. without lysis occurring should be determined for each individual recombinant lysogen. After incubation, the cells would be harvested in a Beckman J. A.-ten rotor at 5,000 r.p.m. for 5 minutes 27°-37° C. The cells would then be rapidly resuspended in 1/20 to 1/50 of the original culture volume in a buffer suitable for protein and the resuspended cells are rapidly frozen in liquid nitrogen. When the frozen cells are thawed, essentially complete lysis of the induced lysogen results.

If crude antigen is required, the crude lysate described above could be used. However, if pure antigen is needed, the beta-galactosidase fusion protein would be purified by any of a number of methods known to those of skill in the art. The most rapid method of purification takes advantage of the size of the beta-galactosidase fusion protein (approximately 114 kDa). Since only a few proteins in *E. coli* are larger than beta-galactosidase, the fusion protein is often resolved from other proteins on SDS-polyacrylamide gels. Preparative gels could be used to isolate large quantities of denatured protein. If pure antigen in native form is required, then the fusion protein could be prepared by classical column chromatography.

G. Synthesis Of A Synthetic Peptide Containing The Amino Acid Cytadhesin Epitope The following prophetic example describes methods for preparing synthetic polypeptides containing cytadhesin epitopes. *M. pneumoniae* P1 polypeptides could be prepared by any of a number of methods known to those of skill in the art. These methods include but are not limited to solid and liquid phase chemical synthesis and biological in vitro synthesis. For example, see Marglin and Merrifield, *Annu. Red. Biochem.*, 39:841-866 (1970); Merrifield, et al., *Biochemistry*, 21:5020-5031 (1982); Pelham and Jackson, *Eru. J. Biochem.*, 67:247-256 (1976); and Shinnick, et al., *Ann. Rev. Microbiol.*, 37:425-446 (1983), all incorporated herein by reference. Of course, where an mRNA translation system is used, e.g., reticulocyte lysate system, it is important to prepare mRNA from the DNA clones of the present invention. Techniques for preparing the mRNA from DNA clones are known in the art. For example, see those described in Chapter 2, 1987 Promega Biological Research Products Catalogue, obtainable from Promega Biolabs, 2800 South Fish Hatchery Road, Madison, Wis. 53711-5305 and incorporated herein by reference. A preferred method for preparing a synthetic peptide may be found in Nestor, Jr., et al. U.S. Pat. No. 4,493,795, and incorporated herein by reference. A second method is found in Arman, et al. U.S. Pat. No. 4,474,757, and also incorporated herein by reference.

H. Preparation Of *M. pneumoniae* Compositions For Use As *M. pneumoniae* Vaccines Of course, it is also likely that the cytadhesin peptides may be effectively used as vaccines to prevent atypical pneumoniae caused by *M. pneumoniae.* The preparation of vaccines which contain peptide sequences as active ingredients is generally well understood in the art, as exemplified by U.S. Pat. Nos.: 4,474,757; 4,493,795; 4,608,251; 4,601,903; 4,599,231; 4,599,230; 4,596,792; and 4,578,770, all incorporated herein by reference.

This prophetic example describes preparation and administration of such vaccines. In general, immunogenic compositions suitable for administration as vaccines could be formulated to include one or more of the antigenic epitopes produced by the recombinant cells of the present invention or synthetically prepared. The antigens could be included in optimal amounts, for example, approximately equimolar or equi-antigenic amounts. Typically, such vaccines are prepared as injectables: either as liquid solutions or suspensions, solid forms suitable for solution in, or suspension in, liquid prior to injection may also be prepared. The preparation could also be emulsified. The reactive immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine could contain minor amounts of auxiliary substances such as wetting or emulsifying agents, pH buffering agents, or adjuvants which enhance the effectiveness of the vaccine.

In addition, immunogenicity of cytadhesin peptides could be increased by conjugation of a carrier molecule, for example, dipalmityl lysine. (See Hopp, *Mol. Immunol.*, 21:13-16 (1984) incorporated herein by reference.)

The proteins or polypeptides could be formulated into the vaccine as neutral or salt forms and administered in a manner compatible with the dosage formulation, and in such amount as will be therapeutically effective and immunogenic. The vaccines could be conventionally administered parenterally, by injection, for example, either subcutaneously or intramuscularly. Additional formulations which are suitable for other modes of administration might include oral or intranasal formulations. The quantity to be administered will depend on the subject to be treated, capacity of the immune system to synthesize antibodies, and the degree of protection desired. Precise amounts of active ingredient required to be administered will depend on the judgment of the practitioner and may be peculiar to each individual. However, suitable dosage ranges will be on the order of 1 to 100 ug active ingredient per individual. Suitable regimes for initial administration and booster shots will also be variable, but may be typified by an initial administration followed by subsequent inoculations or other administrations.

In many instances, it may be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the antigens as described below.

I. Immunoassay For *M. pneumoniae* Antibodies

As demonstrated by Example IV E., certain of the P1 polypeptides are known to react with antisera from patients infected with *M. pneumoniae*. Accordingly, these polypeptides may be used as antigens in immunoassay procedures. These assays are well known to those of skill in the art. For examples of such assays, see Nisonoff, *Introduction to Molecular Immunology*, 2nd Ed., Sinaues Associates, Inc., Sunderland, Mass. (1984) and U.S. Pat. No. 4,376,110, both incorporated herein by reference.

The following prophetic example is designed to illustrate such procedures. Generally, for detection of antibody in aqueous samples, the antigen, or antigen composition, is preferably adsorbed, or otherwise attached, to an appropriate adsorption matrix, for example, the inside surface of a microtiter dish well, and an aqueous suspected antibody-containing composition contacted therewith to cause immunocomplex formation. The matrix is then washed to remove non-specifically bound material and the amount of material which is specifically immunocomplexed thereto determined, typically through the use of an appropriate labeled ligand.

The cytadhesin polypeptides provided by the present invention may also be incorporated into a diagnostic kit. Such kits are widely used in clinical settings because they often offer greater convenience and simplicity than other assays. A number of kits might be utilized in the practice of the present invention, for example, a kit comprising a carrier compartmentalized to receive at least one, at least two, or at least three or more containers and to maintain said containers enclosed confinement.

A first container might include one or more of the *M. pneumoniae* antigens, or antigen-containing compositions. Alternatively, or in addition, the kits will include antibody compositions having specificity for one or more of the antigens. Both antibody and antigen preparations should preferably be provided in a suitable titrated form, with antigen concentrations and/or antibody titers given for easy reference in quantitative applications.

The kits will also typically include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for the antigen or first antibody. Thus, the reaction is detected or quantified by means of detecting or quantifying the label. Immunodetection reagents and processes suitable for application in connection with the novel compositions of the present invention are generally well known in the art.

The foregoing description has been directed to particular embodiments of the invention in accordance with the requirements of the Patent Statutes for the purposes of illustration and explanation. It will be apparent, however, to those skilled in this art, that many modifications and changes in the apparatus and procedure set forth will be possible without departing from the scope and spirit of the invention. It is intended that the following claims be interpreted to embrace all such modifications and changes.

What is claimed is:

1. A substantially purified nucleic acid molecule comprising a nucleotide sequence encoding a *M. pneumoniae* P1 protein or a C-terminal portion thereof.

2. The nucleic acid molecule of claim 1 wherein said *M. pneumoniae* P1 protein has a molecular weight between about 160 kDa and about 175 kDa.

3. The nucleic acid molecule of claim 1 wherein the nucleotide sequence is defined further as a nucleotide sequence encoding at least a translated portion of the amino acid sequence of FIG. 6.

4. A substantially purified nucleic acid molecule comprising a nucleotide sequence encoding an *M. pneumoniae* P1 polypeptide having a cytadhesin epitope.

5. The nucleic acid molecule of claim 4 wherein the protein or polypeptide is capable of immunospecifically binding to monoclonal antibody 6E7, produced by ATCC #HB 8420.

6. The nucleic acid molecule of claim 4 wherein the protein or polypeptide is capable of immunospecifically binding to monoclonal antibody 5B8, produced by ATCC #HB 9586.

7. A substantially purified nucleic acid molecule comprising a nucleotide sequence encoding a polypeptide of at least thirteen contiguous amino acids in length, said polypeptide included in *M. pneumoniae* P1 protein.

8. The nucleic acid molecule of claim 7 wherein the polypeptide comprises the following amino acid sequence:

Gly - Ile - Val - Arg - Thr - Pro - Leu - Ala - Glu - Leu - Leu - Asp - Gly.

9. The nucleic acid molecule of claim 7 wherein the polypeptide comprises the following amino acid sequence:

Asn - Thr - Asn - Thr - Gly - Asn - Asp - Val - Val - Gly - Val - Gly - Arg - Leu - Ser - Glu - Ser - Asn - Ala - Ala - Lys - Met - Asn - Asp - Asp - Val - Asp - Gly - Ile - Val - Arg - Thr - Pro - Leu - Ala - Glu - Leu - Leu - Asp - Gly.

10. The nucleic acid molecule of claim 7 wherein the polypeptide comprises the following amino acid sequence:

Gly - Ile - Val - Arg - Thr - Pro - Leu - Ala - Glu - Leu - Leu - Asp - Gly - Glu - Gly - Gln - Thr - Ala - Asp - Thr - Gly - Pro - Gln - Ser - Val - Lys - Phe -Lys - Ser - Pro - Asp - Gln - Ile - Asp - Phe - Asn - Arg - Leu - Phe - Thr - His - Pro - Val - Thr - Asp - Leu - Phe - Asp - Pro - Val - Thr - Met - Leu - Val - Tyr - Asp - Gln - Tyr - Ile - Pro - Leu - Phe - Ile - Asp - Ile - Pro - Ala - Ser - Val - Asn - Pro - Lys - Met - Val - Arg - Leu - Lys - Val - Leu - Ser - Phe - Asp - Thr - Asn - Glu - Gln - Ser - Leu - Gly - Leu - Arg - Leu - Glu - Phe - Phe - Lys - Pro - Asp - Gln - Asp - Thr - Gln - Pro - Asn - Asn - Asn - Val - Gln - Val - Asn - Pro - Asn - Asn - Gly - Asp - Phe - Leu - Pro - Leu - Leu - Thr - Ala - Ser - Ser - Gln - Gly - Pro - Gln - Thr - Leu - Phe - Ser - Pro - Phe - Asn - Gln.

11. The nucleic acid molecule of claim 7 wherein the polypeptide comprises the following amino acid sequence:

Asp - Thr - Gly - Pro - Gln - Ser - Val - Lys - Phe -Lys - Ser - Pro - Asp - Gln - Ile - Asp - Phe - Asn - Arg - Leu - Phe - Thr - His - Pro - Val - Thr - Asp - Leu - Phe - Asp - Pro - Val - Thr - Met - Leu - Val - Tyr - Asp - Gln - Tyr - Ile - Pro - Leu - Phe - Ile - Asp - Ile - Pro - Ala - Ser - Val - Asn - Pro - Lys - Met - Val - Arg - Leu - Lys - Val - Leu - Ser - Phe - Asp - Thr - Asn - Glu - Gln - Ser - Leu - Gly - Leu - Arg - Leu - Glu - Phe - Phe - Lys - Pro - Asp - Gln - Asp - Thr - Gln - Pro - Asn - Asn - Asn - Val - Gln - Val - Asn - Pro - Asn - Asn - Gly - Asp - Phe - Leu - Pro - Leu - Leu - Thr - Ala - Ser - Ser - Gln - Gly - Pro - Gln - Thr - Leu - Phe - Ser - Pro - Phe - Asn -Gln.

12. The nucleic acid molecule of any one of claims 1-11 defined further as being DNA.

13. A recombinant nucleotide vector comprising the nucleic acid sequence of claim 12.

14. A bacterial cell comprising the recombinant vector of claim 13.

15. The bacterial cell of claim 14 further defined as *E. coli*.

16. A substantially purified DNA molecule comprising a nucleotide sequence which includes at least a tetradecameric portion of contiguous nucleotides of the DNA sequence of FIG. 6.

17. The DNA molecule of claim 16 wherein the nucleotide sequence comprises nucleotides 178 to 190 of the nucleotide sequence of FIG. 6

18. The DNA molecule of claim 16 wherein the nucleotide sequence comprises nucleotides 196 to 213 of the nucleotide sequence of FIG. 6.

19. The DNA molecule of claim 16 wherein the nucleotide sequence comprises nucleotides −90 to 258 of the nucleotide sequence of FIG. 6

20. The DNA molecule of claim 16 wherein the nucleotide sequence comprises nucleotides −204 to 911 of the nucleotide sequence of FIG. 6.

21. The DNA molecule of claim 16 wherein the nucleotide sequence comprises nucleotides 4148 to 4881 of the nucleotide sequence of FIG. 6

22. The DNA molecule of claim 16 wherein the nucleotide sequence comprises nucleotides 4202 to 4881 of the nucleotide sequence of FIG. 6.

23. The DNA molecule of claim 16 wherein the nucleotide sequence comprises nucleotides 4067 to 4185 of the nucleotide sequence of FIG. 6.

24. The DNA molecule of claim 16 wherein the nucleotide sequence comprises nucleotides 4148 to 4185 of the nucleotide sequence of FIG. 6.

25. The DNA molecule of claim 16 wherein the nucleotide sequence comprises at least a coding region of the nucleotide sequence of FIG. 6.

26. The DNA molecule of claim 16 wherein the nucleotide sequence comprises the nucleotide sequence of FIG. 6.

27. The DNA molecule of any one of claims 16-25 wherein the DNA molecule is capable of hybridizing to a recombinant insert of plasmid pMPN P1, ATCC #67560 (pending).

28. The DNA molecule of claim 27 wherein the hybridization conditions are further defined as moderately stringent.

29. The DNA molecule of claim- 28 wherein the hybridization conditions are defined as stringent.

30. A recombinant DNA vector comprising the DNA molecule of any one of claims 16-26 and 28-29..

31. A bacterial cell comprising the recombinant vector of claim 30.

32. The bacterial cell of claim 31 further defined as *E. Coli.*

33. A method for isolating mycoplasmal DNA comprising:
(a) fragmenting mycoplasmal DNA to produce DNA restriction fragments;
(b) separating the DNA restriction fragments according to their sizes or molecular weights;
(c) hybridizing the DNA restriction fragments with a DNA molecule as defined by any one of claims 16-29; and
(d) identifying at least one restriction fragment which hybridizes to said DNA molecule by means of a label.

34. The method of claim 33 wherein the mycoplasmal DNA is *M. genitalium* DNA.

35. The method of claim 33 wherein separating the DNA restriction fragments is by electrophoresis through a gel matrix.

36. The method of claim 33 wherein the mycoplasmal DNA is fragmented with a restriction endonuclease.

37. The method of claim 33 wherein the mycoplasmal DNA is *M. pneumoniae* DNA.

38. The method of claim 33 wherein the label is a radioactive label and hybridization is determined by autoradiography.

39. The method of claim 33 wherein the hybridization is performed using moderately stringent hybridization conditions.

40. The method of claim 33 wherein the hybridization is performed using stringent hybridization conditions.

41. A DNA molecule comprising a recombinant DNA vector which includes the recombinant insert of plasmid pMPN P1, ATCC #67560 or lambda gt11 phage P1-7, P1-9 or P1-10, ATCC #40386, 40385, or 40384, respectively.

42. A bacterial strain comprising a recombinant DNA vector which includes the recombinant insert of pMPN P1, ATCC #67560 or lambda gt11 phage P1-7, P1-9 or P1-10, ATCC #40386, 40385 or 40384, respectively.

43. A substantially purified DNA molecule comprising a nucleotide sequence which includes at least a tetradecameric portion of the DNA sequence of FIG. 6, wherein the DNA molecule is capable of hybridizing to a recombinant insert of plasmid pMPN P1, ATCC #67560 under selected hybridization conditions and is suitable for use as a hybridization probe.

44. A recombinant DNA vector comprising the DNA molecule of claim 27.

* * * * *

UNITED STATES PATENT AND TRADEMARK OFFICE
CERTIFICATE OF CORRECTION

PATENT NO. : 5,026,636
DATED : JUNE 25, 1991
INVENTOR(S) : BASEMAN et al.

It is certified that error appears in the above-identified patent and that said Letters Patent is hereby corrected as shown below:

In column 13, line 23, please replace "tis" with
-- this --.

In column 15, line 4, please replace "EOTA." with
-- EDTA --.

In column 21, line 40, please replace "$\leq 10^5$" with
-- $\leq 10^5$ --.

Signed and Sealed this

Sixteenth Day of March, 1993

Attest:

STEPHEN G. KUNIN

Attesting Officer

Acting Commissioner of Patents and Trademarks